United States Patent
Yick et al.

(10) Patent No.: US 10,064,705 B2
(45) Date of Patent: Sep. 4, 2018

(54) SELF-LIGATING ORTHODONTIC BRACKET

(71) Applicant: 3M INNOVATIVE PROPERTIES COMPANY, St. Paul, MN (US)

(72) Inventors: Lee C. Yick, Placentia, CA (US); Ming-Lai Lai, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/651,726

(22) Filed: Jul. 17, 2017

(65) Prior Publication Data

US 2017/0312054 A1 Nov. 2, 2017

Related U.S. Application Data

(63) Continuation of application No. 14/416,113, filed as application No. PCT/US2013/028785 on Mar. 4, 2013, now Pat. No. 9,730,770.

(60) Provisional application No. 61/674,620, filed on Jul. 23, 2012.

(51) Int. Cl.
*A61C 7/28* (2006.01)

(52) U.S. Cl.
CPC ......... *A61C 7/287* (2013.01); *Y10T 29/49568* (2015.01)

(58) Field of Classification Search
CPC ........... A61C 7/287; A61C 7/34; A61C 7/148; A61C 7/28
See application file for complete search history.

(56) References Cited

U.S. PATENT DOCUMENTS

| | | |
|---|---|---|
| 4,978,007 A | 12/1990 | Jacobs |
| 5,015,180 A | 5/1991 | Randklev |
| 5,322,435 A | 6/1994 | Pletcher |
| 5,366,372 A | 11/1994 | Hansen |
| 5,429,229 A | 7/1995 | Chester |
| 5,466,151 A | 11/1995 | Damon |
| 6,071,118 A | 6/2000 | Damon |
| 6,183,249 B1 | 2/2001 | Brennan |
| 6,302,688 B1 | 10/2001 | Jordan |
| 6,506,049 B2 | 1/2003 | Hanson |

(Continued)

FOREIGN PATENT DOCUMENTS

| | | |
|---|---|---|
| CN | 201617965 | 3/2010 |
| DE | 10-2008-060820 | 6/2010 |

(Continued)

OTHER PUBLICATIONS

International Search Report for PCT International Application No. PCT/US2013/028785, dated Jul. 23, 2013, 4pgs.

*Primary Examiner* — Nicholas Lucchesi

(57) ABSTRACT

Appliances and related methods use a resilient retention member that is retained in a recess within a body that is optionally made from a suitably translucent ceramic material. The retention member, optionally in combination with one or more side walls of the recess, provides two or more regions for accommodating a protrusion. The protrusion, in turn, is part of a sliding door which can be opened or closed depending on the equilibrium position of the protrusion with respect to the two or more regions. Based on the engagement between the protrusion and the retention member, these appliances can provide discrete opened and closed door positions to facilitate archwire ligation.

16 Claims, 20 Drawing Sheets

(56) References Cited

U.S. PATENT DOCUMENTS

| | | |
|---|---|---|
| 6,582,226 B2 | 6/2003 | Jordan |
| 6,648,638 B2 | 11/2003 | Castro |
| 7,137,812 B2 | 11/2006 | Cleary |
| 7,416,408 B2 | 8/2008 | Farzin-Nia |
| 7,704,072 B2 | 4/2010 | Damon |
| 8,033,824 B2 | 10/2011 | Oda |
| 8,636,508 B2 | 1/2014 | Forster |
| 8,998,607 B2* | 4/2015 | Oda .................. A61C 7/30 433/10 |
| 9,277,973 B2* | 3/2016 | Damon ............... A61C 7/287 |
| 2005/0239012 A1 | 10/2005 | Bathen |
| 2007/0248928 A1 | 10/2007 | Damon |
| 2008/0286710 A1 | 11/2008 | Cinader, Jr. |
| 2009/0004618 A1 | 1/2009 | Oda |
| 2009/0155734 A1 | 6/2009 | Damon |
| 2009/0298003 A1 | 12/2009 | Wei |
| 2010/0055626 A1 | 3/2010 | Endou |
| 2010/0055636 A1 | 3/2010 | Yeh |
| 2010/0178629 A1* | 7/2010 | Oda .................. A61C 7/125 433/14 |
| 2010/0196838 A1* | 8/2010 | Damon ............... A61C 7/287 433/10 |
| 2010/0285420 A1 | 11/2010 | Oda |
| 2011/0086323 A1 | 4/2011 | Wessinger |
| 2011/0318699 A1 | 12/2011 | Forster |
| 2012/0141948 A1* | 6/2012 | Farzin-Nia ............ A61C 7/20 433/11 |
| 2013/0189638 A1* | 7/2013 | Oda .................. A61C 7/287 433/10 |
| 2013/0330683 A1* | 12/2013 | Wang ................ A61C 7/287 433/11 |
| 2014/0205960 A1* | 7/2014 | Farzin-Nia ............ A61C 7/20 433/10 |
| 2014/0242533 A1* | 8/2014 | Yeh .................. A61C 7/287 433/11 |
| 2014/0272753 A1* | 9/2014 | Sommer .............. A61C 7/287 433/11 |
| 2015/0017597 A1* | 1/2015 | Solano Reina ........ A61C 7/14 433/10 |

FOREIGN PATENT DOCUMENTS

| | | |
|---|---|---|
| JP | 2008052159 | 3/2008 |
| WO | WO 2013-055529 | 4/2013 |

\* cited by examiner

SELF-LIGATING ORTHODONTIC BRACKET

FIELD OF THE INVENTION

Provided are appliances and related methods used in orthodontic treatment. More particularly, the provided appliances and methods relate to orthodontic appliances that are self-ligating.

BACKGROUND

Orthodontics is a field of dentistry associated with the professional supervision, guidance and correction of mal-positioned teeth. The benefits of orthodontic treatment include attaining and maintaining a proper bite function, enhancing facial aesthetics, and improving dental hygiene. To achieve these goals, the orthodontic professional often makes use of corrective appliances that engage to the patient's teeth and apply gentle therapeutic forces to move the teeth toward proper positions.

One common type of treatment uses tiny slotted appliances called orthodontic brackets, which are adhesively attached to either the front or back surfaces of the teeth. To begin treatment, a resilient arch-shape wire ("archwire") is received into the slot of each bracket. The ends of the archwire are generally captured in appliances called molar tubes, which are affixed to the patient's molar teeth. As the archwire slowly returns to its original shape, it acts as a track that guides the movement of teeth toward desired positions. The brackets, tubes, and archwire are collectively known as "braces."

The procedure used to engage and activate the archwire on the orthodontic bracket is known as ligation. Traditional brackets are ligated to the archwire with the help of one or more pairs of opposing tiewings, or cleat-like projections on the bracket body. The archwire is placed in the archwire slot and generally a tiny elastomeric "O"-ring ligature, or alternatively metal ligature wire, is tightened over the archwire and under the undercut portions of tiewings located on opposite sides of the archwire slot. The ligature thus secures the archwire within the archwire slot of each bracket and provides a precise mechanical coupling between these bodies.

Ligatures have numerous drawbacks. For example, elastomeric ligatures have a tendency to lose their elasticity over time, resulting in inconsistent archwire sliding mechanics. While these ligatures can be made translucent for aesthetic treatment, they also tend to easily stain. Ligation using a ligature wire, on the other hand, can be quite cumbersome and time-consuming. Being made of metal, ligature wire is also generally considered non-aesthetic.

Self-ligating brackets present a solution to the above problems. These appliances generally use a clip, spring member, door, shutter, bail, or other ligation mechanism built into the bracket itself to retain the archwire in the slot, thereby obviating use of a separate ligature. Several advantages can derive from the use of self-ligating brackets. For example, these appliances can decrease friction between the archwire and the bracket compared with brackets ligated with elastomeric ligatures, potentially providing faster leveling and aligning of teeth in early stages of treatment. Depending on the ligation mechanism, these appliances can also simplify the installation and removal of an archwire, significantly reducing chair time for the treating professional. Finally, self-ligating brackets can also provide better hygiene than conventional brackets, which use elastomeric ligatures and ligature wires that can trap food and plaque.

SUMMARY

The realization of an aesthetic self-ligating bracket poses a number of technical challenges and tradeoffs. For example, the material used in a clip, spring member, door, bail, or other ligation mechanism is typically metallic, and strongly contrasts with the natural color of teeth. While polymeric materials are aesthetic and can be configured for this function, polymers are generally soft, vulnerable to wear, and stain easily during the course of treatment. Finally, ceramic materials have long been known to provide reasonable strength, resistance to staining, and excellent aesthetics. However, these materials are also brittle, can be difficult to machine and assemble, and do not have the resiliency needed for most ligation mechanisms.

The provided appliances and related methods overcome this dilemma by using a ligation mechanism that can be embedded within an aesthetic appliance assembly. In an exemplary embodiment, these appliances use a retention member located in a recess of a ceramic body. The retention member, optionally in combination with one or more side walls of the recess, provides a plurality of regions for accommodating a protrusion. The protrusion, in turn, is part of a door slidably engaged to the body and can be opened or closed depending on the equilibrium position of the protrusion with respect to the two or more regions. Based on the engagement between the protrusion and the clip, these appliances can provide discrete, pre-defined opened and closed door positions, thereby facilitating archwire ligation for the treating professional.

In one aspect, an orthodontic appliance is provided. The appliance comprises: a base; a body extending outwardly from the base; an archwire slot extending across the body in a generally mesial-distal direction; a recess located on the body adjacent the archwire slot; a retention member received in the recess, the retention member dividing the recess into at least first and second regions; and a door slidably engaged to the body and having a protrusion, the protrusion extending into the first region when the door is open to allow access to the archwire slot and extending into the second region when the door is closed to prevent access to the archwire slot.

In another aspect, an orthodontic appliance comprising: a base; a body extending outwardly from the base; an archwire slot extending across the body in a generally mesial-distal direction; a recess located on the body adjacent the archwire slot, the recess having a bottom wall and opposing first and second side walls; a retention member received in the recess; and a door slidably engaged with the body and having a protrusion extending into the recess, the retention member resiliently deflecting to toggle the protrusion between a first position wherein the door is open to allow access to the archwire slot and a second position wherein the door is closed to prevent access to the archwire slot.

In yet another aspect, an orthodontic appliance is provided, comprising: a base; a body extending outwardly from the base; an archwire slot extending across the body in a generally mesial-distal direction; a recess located on the body adjacent the archwire slot, the recess having a bottom wall and opposing first and second side walls; a retention member received in the recess, the retention member comprising: a center section extending along the bottom wall and having first and second ends; an arched section joined to the first end and having an apex; and a tail section joined to the second end and extending at an acute angle relative to the center section; and a door slidably engaged with the body and having a protrusion extending into the recess, wherein the protrusion resides between the first side wall and the arched section when the door is open to allow access to the archwire slot and the protrusion rests between the arched section and the second side wall when the door is closed to prevent access to the archwire slot.

In yet another aspect, a method is provided for assembling an orthodontic appliance having ceramic body, a ceramic door having a protrusion, and a retention member. The method comprises: placing the retention member into a recess located in the body; slidably engaging the door along a pair of rails disposed on the body until the protrusion contacts an exterior surface of the retention member; and urging the door against the retention member until the protrusion is received within a region of the recess that is at least partially defined by the combination of the recess and an interior surface of the retention member.

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION

The following sections further describe particular embodiments of the invention directed to orthodontic appliances, kits, and methods of assembling the same. The illustrated embodiments in this disclosure are exemplary only and should not be construed to unduly limit the invention. For example, one of ordinary skill can adapt the disclosed appliances, kits, and methods for attachment to either the facial or lingual surfaces of teeth, to different teeth within the same dental arch, and to teeth of either the upper or lower dental arches. The appliances, kits, and methods described herein may also either be customized or non-customized to the individual patient undergoing treatment. Preferred embodiments include appliance components that are made from a translucent ceramic for improved aesthetics. Notwithstanding, material and dimensional specifications and intended methods of use could vary, even significantly, from those disclosed herein without departing from the scope of the claimed invention.

Figure 1:
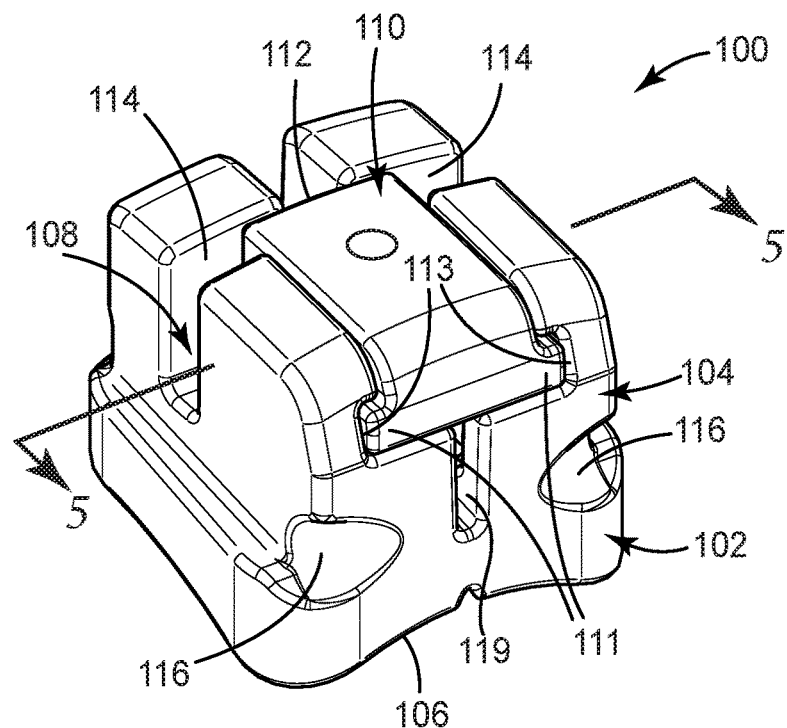
FIG. 1 is a perspective view of an orthodontic appliance according to one embodiment, looking toward its facial, occlusal, and mesial sides.
Figure 2:
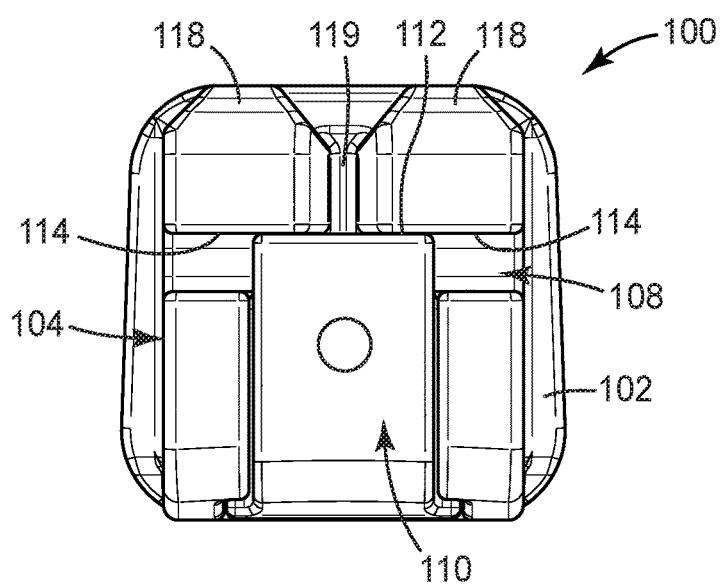
FIG. 2 is a plan view of the appliance of FIG. 1, looking toward its facial side.

An orthodontic appliance according to one embodiment, designated by the numeral 100, is shown in FIGS. 1 and 2 in assembled form. The appliance 100 has a base 102 and a body 104 extending outwardly from the base 102. The bottom of the base 102 has a bonding surface 106 having a concave three-dimensional surface contour generally matching that of a respective tooth to which the appliance 100 is to be bonded. The bonding surface 106 can optionally have holes, grooves, recesses, undercuts, partially embedded particles, mesh, a chemical bond enhancement material, a micro-etched surface, or any other material, structure, or combination thereof, to facilitate adhesive bonding of the appliance 100 to a tooth surface.

An archwire slot 108, having a generally rectilinear configuration, extends in a generally mesial-distal direction across a generally facial-facing surface of the body 104. Controlling access to the archwire slot 108 is a door 110, which is slidably received in the body 104 and shown in its closed position in FIGS. 1-2. In this particular embodiment, the door 110 has a pair of rails 111, each extending along a generally occlusal-gingival direction on the mesial and distal sides of the door 110. The rails 111 slide along a pair of opposing complementary grooves 113 disposed in the body 104. There may be appropriate tolerances between the rails 111 and the grooves 113 to facilitate sliding of the door 110 and avoid binding. A portion of the door 110 extends across a central portion of the archwire slot 108, thereby preventing ingress or egress of an archwire (not shown here) with respect to the slot 108 of the appliance 100. Optionally and as shown, the leading edge 112 of the door 110 abuts against the gingival side wall 114 of the archwire slot 108 when the door 110 is closed.

Again referring to FIGS. 1-2, the door 110 is capable of sliding both occlusal and gingival directions to toggle between an open position allowing access to the archwire slot 108 and a closed position preventing access to the archwire slot 108. Under most circumstances, the door 110 is adequate on its own to ligate an archwire to the appliance 100. If desired, however, a treating professional can elect to manually ligate the archwire with the assistance of the undercuts 116 and tiewings 118 located on the body 104. Ligation can be achieved, for example, by securing an elastomeric o-ring or ligature wire beneath the undercuts 116, over an archwire received in the slot 108, and beneath the tiewings 118. The undercuts 116 and tiewings 118 may also be used to secure a power chain to two or more teeth if so desired.

In exemplary embodiments, some or all of the base 102, body 104, and door 110 are made from a translucent ceramic material. Particularly preferred ceramic materials include the fine-grain polycrystalline alumina materials described in issued U.S. Pat. No. 6,648,638 (Castro, et al.). These ceramic materials are known for their high strength and also provide superior aesthetics compared with metallic materials because they transmit light and can visually blend in with the color of the underlying tooth surface.

FIGS. 1-2 also show a vertical groove 119 that extends from the gingival side to the occlusal sides of the facial side of the body 104. The groove 119 runs between the tiewings 118, bifurcating the body 104 into mesial and distal halves. In some embodiments, the vertical groove 119 at least partially defines a frangible web located between the bottom of the groove 119 and the bonding surface 106 and enables the appliance to be conveniently squeeze-debonded by fracturing a frangible web and pivoting the mesial and distal halves of the appliance 100 toward each other. Further options and advantages are described in issued U.S. Pat. No. 5,366,372 (Hansen, et al.).

Various mechanisms can be implemented to toggle the door 110 between discrete positions—for example, between open and closed positions. Mechanisms that provide local equilibrium positions for the door 110 can advantageously prevent the door from spontaneously closing when a treating professional is placing an archwire in the slot 108 or conversely, spontaneously opening during the course of treatment.

Figure 3:
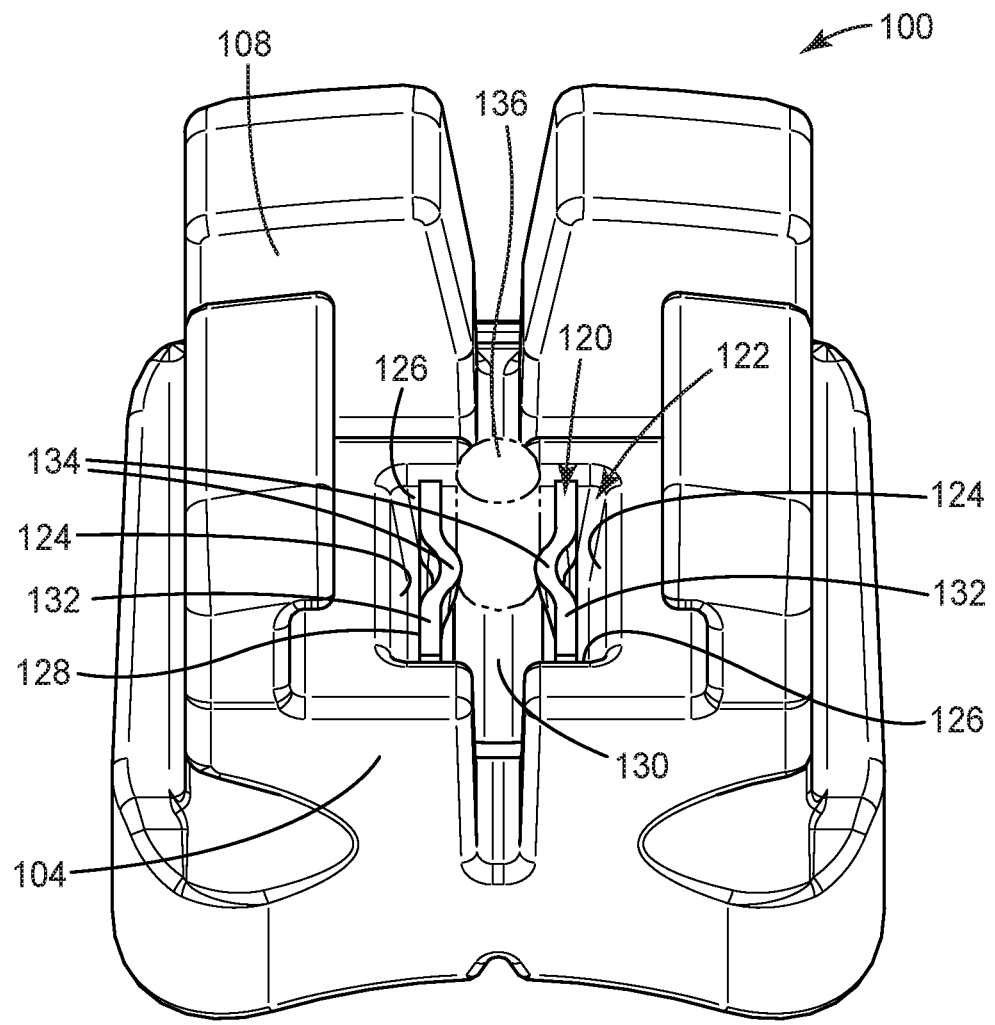
FIG. 3 is a perspective view of the appliance of FIGS. 1-2 with one component removed to show hidden features of the appliance, looking toward its occlusal and facial sides.
Figure 4A:
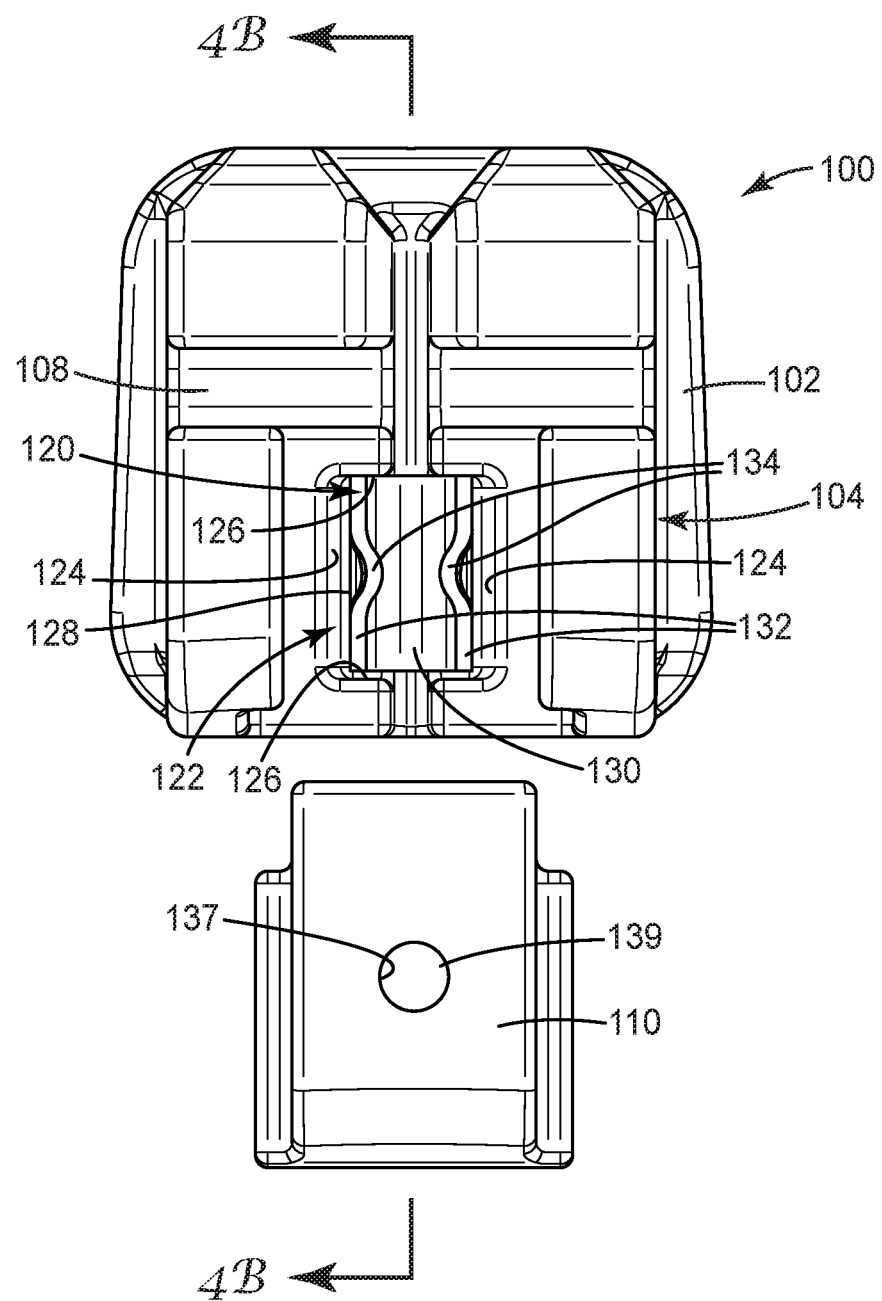
FIG. 4A is a plan view of the appliance of FIGS. 1-3 in a disassembled configuration, looking toward its facial side.
Figure 4B:
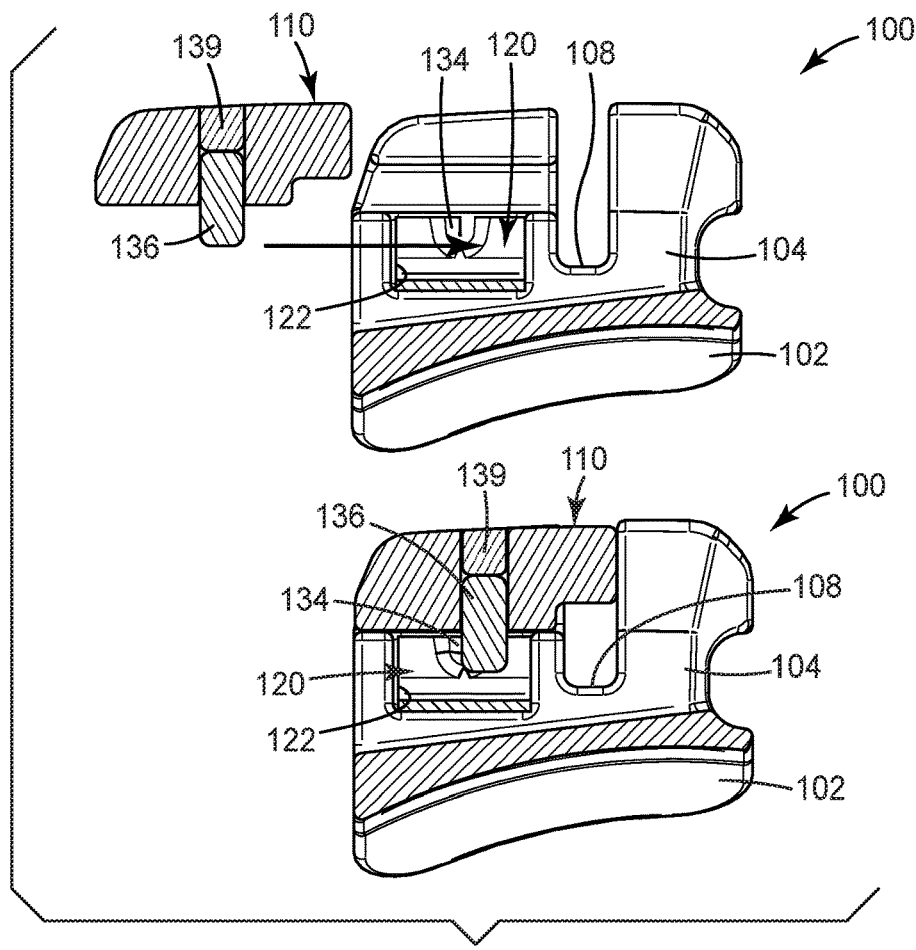
FIG. 4B are a pair of cross-sectional views of the appliance of FIGS. 1-4A in a disassembled and assembled configuration along 4B-4B in FIG. 4A, looking toward mesial-facing cross-sectional surfaces.

FIGS. 3, 4A and 4B shows the clip 120 received in a recess 122 embedded in an overall appliance assembly that includes the door 110 (for clarity, not shown in FIG. 3), body 104, and base 102. The recess 122 is located adjacent the archwire slot 108 and has a generally rectangular shape in plan view, with opposing mesial and distal side walls 124, opposing occlusal and gingival side walls 126 and a bottom wall 128. Although some clearance is provided along all four side walls 124, 126, the inner walls of the recess 122 generally conform to the exterior surfaces of the clip 120 and prevent the clip 120 from substantially moving in lateral directions parallel to the bottom wall 128. It is to be understood that the clip 120 is merely an exemplary retention member, and an alternative retention member having a different geometry or orientation may be substituted for the clip 120 without compromising its function.

The clip 120 has an overall trough-like shape, with a bottom section 130, and a pair of side sections 132. Preferably the clip 120 is made from a resilient material having a high elastic strain limit, such as a shape memory material based on an alloy of nickel and titanium, although other materials such as stainless steel, beta titanium, cobalt alloys (e.g. from Elgiloy Specialty Metals, Elgin, Ill.), or even certain plastic materials may be used. The interior surfaces of the side sections 132 include a pair of opposing inward-facing projections 134. As particularly shown in FIG. 4B, the pair of projections 134, which in this case are centrally located on the clip 120, divides the recess 122 into occlusal and gingival regions 138, 140 that communicate with each other through the narrowed area between the projections 134.

Figure 4C:
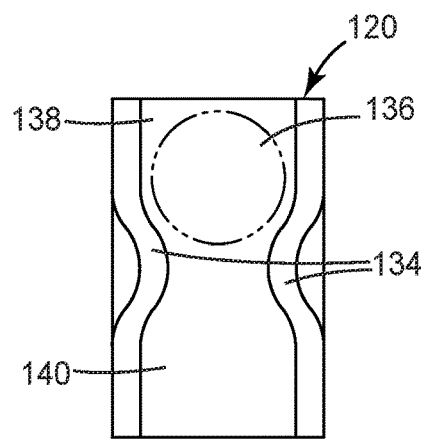
FIG. 4C is a plan view showing interacting components of the appliance of FIGS. 1-4B, looking toward their facial sides.
Figure 5:
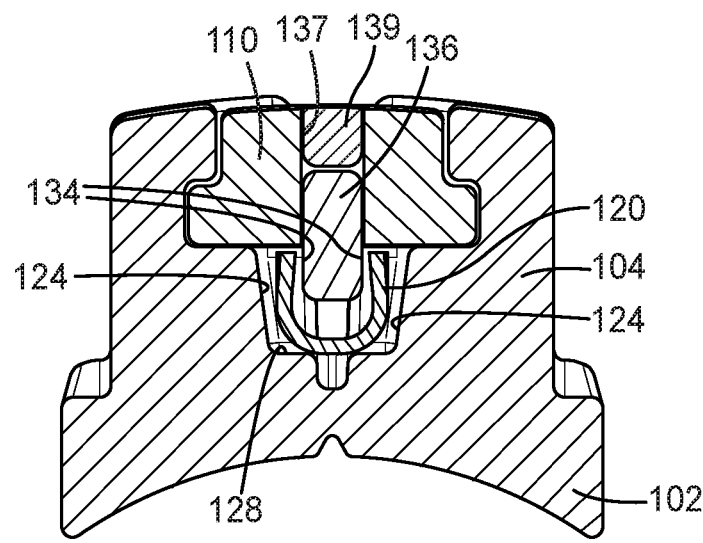
FIG. 5 is a side cross-sectional view of the appliance of FIGS. 1-4C as assembled along 5-5 in FIG. 1, looking toward an occlusal-facing cross-sectional surface.

As further shown in FIG. 4C, a protrusion 136 of the door 110 is located in the gingival region 140. The protrusion 136 can be either an integral or discrete part of the door 110 (remaining parts of the door 110 hidden in FIGS. 3 and 4C) and located such that the position of the protrusion 136 in the recess 122 corresponds to a closed position of the door 110 as shown in FIGS. 1-2. The side walls 124, 126 hold the protrusion 136 captive within the regions 138, 140 and prevent the door 110 from becoming dislodged from the body 104. Unless the door 110 is being actively opened or closed, the protrusion 136 generally assumes one of the two positions defined by the regions 138, 140, corresponding to the closed and open positions of the door 110, respectively.

The door 110 can be assembled to the body 104 in any of a number of different ways. These figures show, for example, the protrusion 136 as a separate component. In this figure, the protrusion 136 is received and retained in an aperture 137 extending through the door 110 in a generally facial-lingual direction, allowing the door 110 to be first slidably engaged with the body 104, and then the protrusion 136 received through the aperture from the facial side of the door 110 to engage the clip 120. For aesthetic reasons, the aperture 137 on the facial side of the door 110 can then be sealed with a suitable aesthetic plug 139 to hide the protrusion 136. In an alternative method of assembly, the clip 120 and protrusion 136 can be inserted together into the door 110 and recess 122 from the lingual direction by means of an enlarged opening in the base 102 (not shown here). The opening can be subsequently patched using a suitably configured plug. In any of the above embodiments, the protrusion 136 can be joined to the main part of the door 110 using any known methods, including being press fit, brazed or adhesively into the door 110.

In yet another embodiment, the protrusion 136 is an integral component of the door 110. In this case, the door 110 can be slidably engaged to the body 104 by sliding the door 110/protrusion 136 through a temporary opening made in, for example, one of the occlusal-gingival side walls 126 of the recess 122. After the protrusion 136 is received in one of the regions 138, 140, the opening can then be suitably plugged or otherwise sealed as described above to capture the clip 120 and protrusion 136 in the recess 122.

The protrusion 136 need not be a rigid member. In some embodiments, the protrusion is itself somewhat complaint. For example, the protrusion 136 could be a spring-like member such as a hollow tube made from a shape memory alloy and capable of resiliently bending, stretching or compressing as it slides relative to the clip 120. Advantageously, the combination of a resilient clip 120 and resilient protrusion 136 can provide greater design freedom to optimize force characteristics of the door 110. As yet another embodiment, the protrusion 136 is resilient while the clip 120 is substantially rigid.

Figure 6:
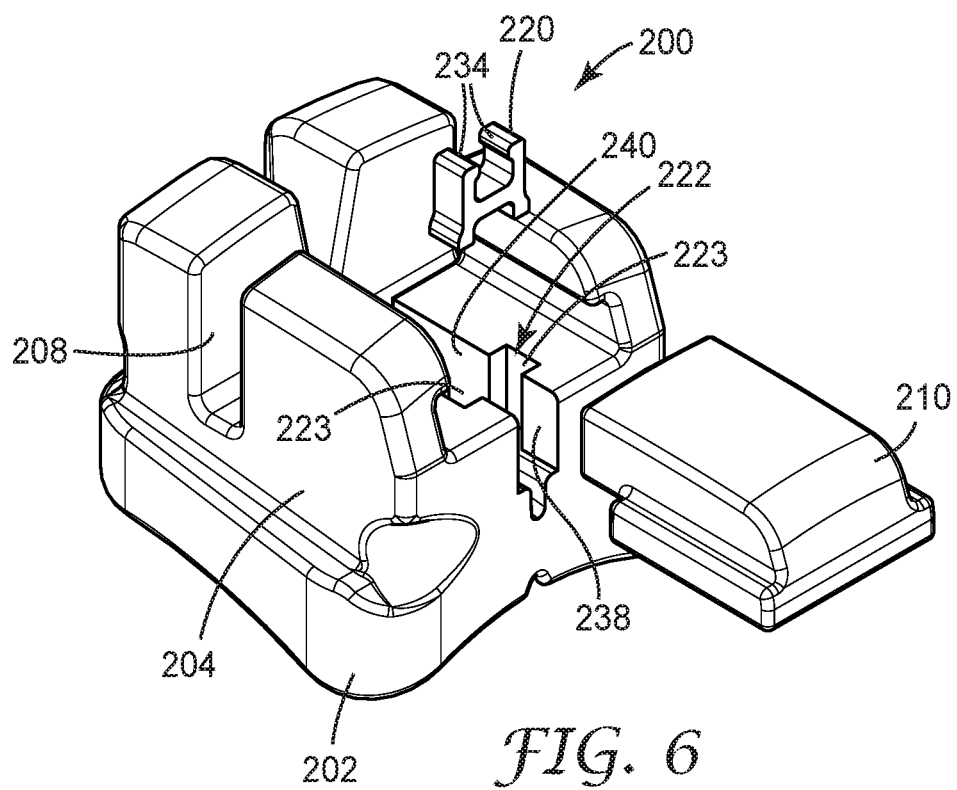
FIG. 6 is an exploded perspective view of an orthodontic appliance according to another embodiment, looking toward its facial, occlusal, and mesial sides.
Figure 6A:
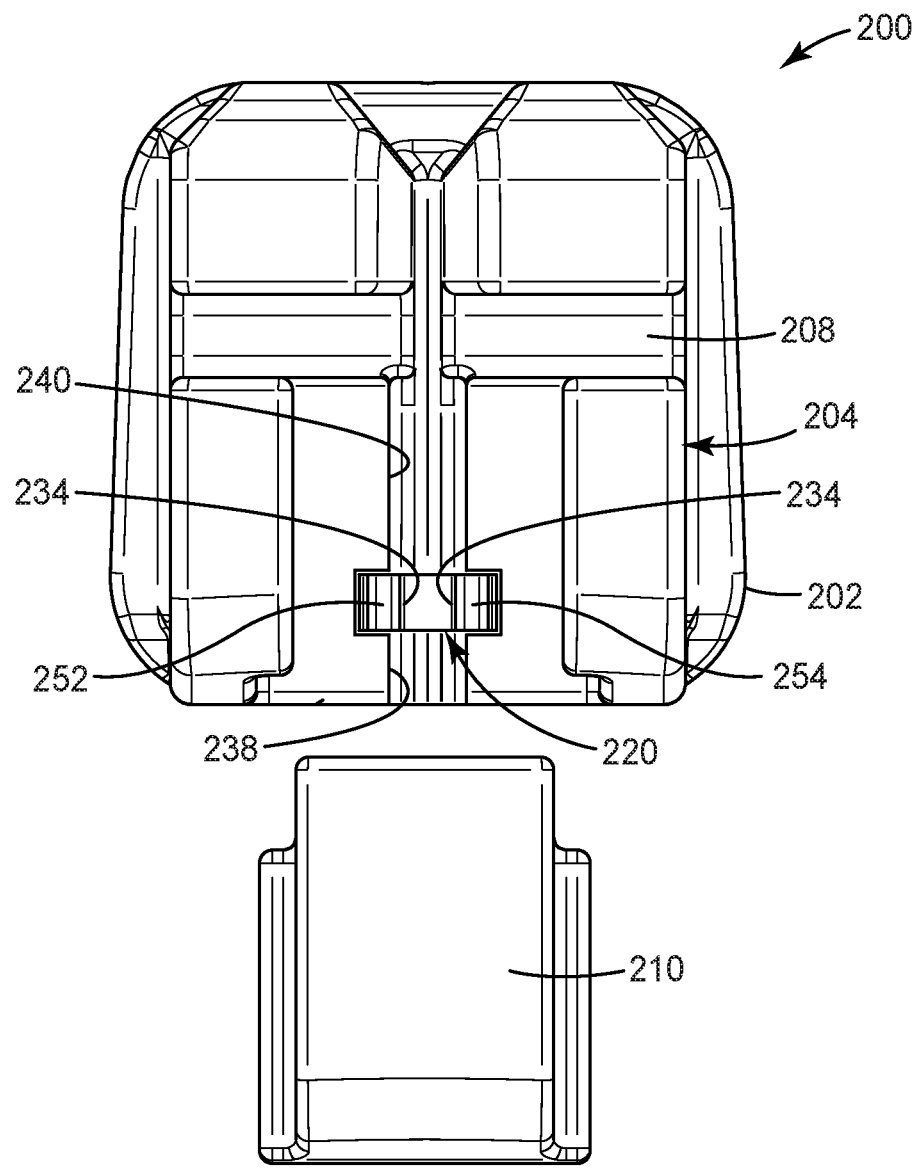
FIG. 6A is an exploded plan view of the orthodontic appliance of FIG. 6, looking toward its facial side.
Figure 7:
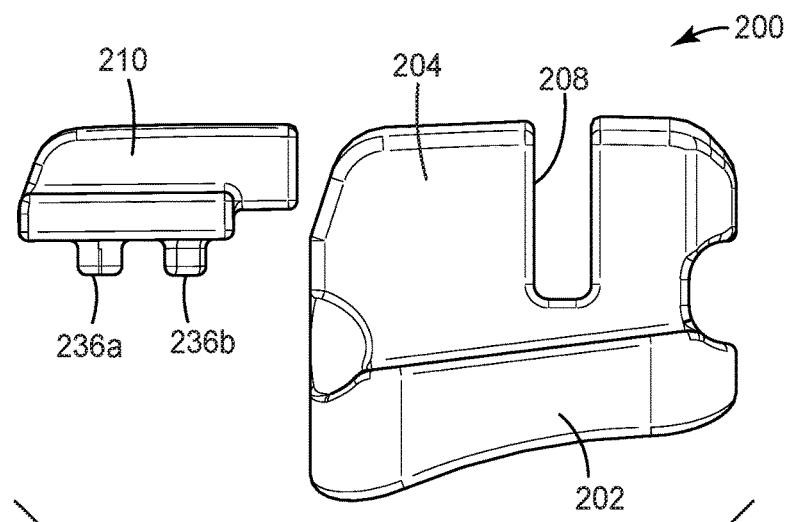
FIG. 7 is side elevational view of the appliance of FIGS. 6-6A in disassembled form, looking toward its distal side.
Figure 8:
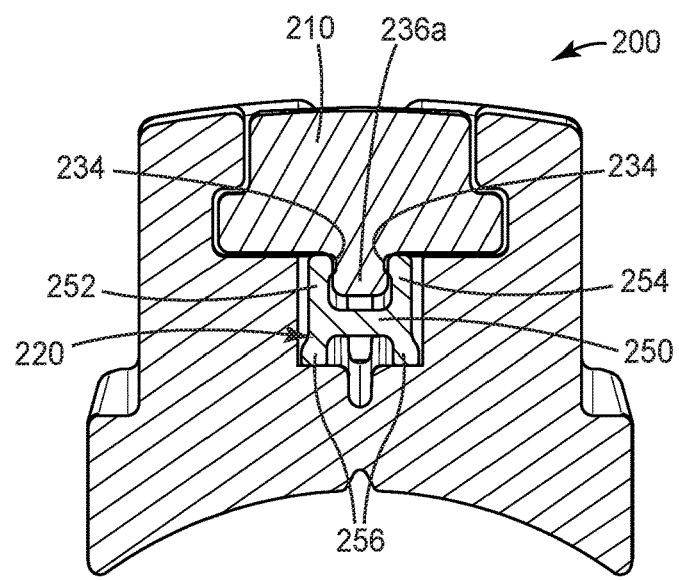
FIG. 8 is a side cross-sectional view of the appliance of FIGS. 6-7 in assembled form, looking toward an occlusal-facing cross-sectional surface.

FIGS. 6-8 show an appliance 200 according to another embodiment. Like the appliance 100 previously described, the appliance 200 has a base 202, a body 204, an archwire slot 208 extending in a mesial-distal direction across the body 204, and a generally cross-shaped recess 222 adjacent the slot 208. Further, a door 210 is slidably engaged to the body 204, where the door 210 includes a pair of protrusions 236a, 236b that extend into the recess 222 when the door 210 is in its closed position. Instead of using a clip with a trough-like configuration, however, the appliance 200 uses an exemplary resilient, planar clip 220 having a generally "H"-shaped configuration as illustrated in FIG. 6. As shown, the clip 220 resides in a reference plane generally perpendicular to an occlusal-gingival axis and generally parallel to the occlusal and gingival walls of the archwire slot 208. The recess 222 has a pair of lateral cutouts 223 that hold the clip 220 captive within the recess 222.

Additional features on the underside of the door 210 are shown in the disassembled view of the appliance 200 in FIG. 7. As shown here, the first and second protrusions 236a, 236b both extend outwardly from the main part of the door 210 toward a generally lingual direction, and are spaced apart from each other along the direction of travel of the door 210.

FIG. 8 shows, in cross-section, the interaction between the door 210 and the clip 220 when the appliance 200 is assembled. In more detail, the clip 220 has a center section 250 and mesial and distal sections 252, 254 joined to respective mesial and distal ends of the center section 250 and extending toward a generally facial direction. The ends of the sections 252, 254 include opposing, inward-facing projections 234. Mesial and distal leg sections 256 are also joined to the mesial and distal terminal ends of the center section 250 and extend toward, and contact, the bottom wall of the recess 222 to provide a stable orientation of the clip 220 in the recess 222.

From the disassembled state, the door 210 can be slidably received in the body 204, resulting in the first protrusion 236a contacting the narrowed area within the recess 222 presented by the inward-facing projections 234, as shown in FIG. 6. At this point, the first protrusion 236a resides in a first region 238 of the recess 222. When sufficient force is applied to the door 210 (here, in a generally gingival direction) then the sections 252, 254 spread apart allowing the first protrusion 236a to pass through and enter a second region 240 of the recess 222 while the second protrusion 236b is now in the first region 238. In this configuration, the door 210 is in its open position.

If force is maintained against the door 210 toward the same direction, then the second protrusion 236b urges against the projections 234 until sufficient force results in the sections 252, 254 again spreading apart and allowing the second protrusion 236b to join the first protrusion 236a in the second region 240. In this relative arrangement, the door 210 is now in its closed position. The protrusions 236a, 236b therefore reside in the first and second regions 238, 240 (on opposite sides of the clip 220) when the door is open, while the protrusions 236a, 236b both reside in the second region 240 (on the same side of the clip 220) when the door is closed.

Figure 7A:
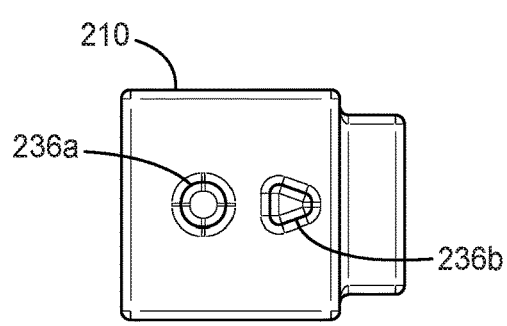
FIG. 7A is a plan view of a component of the appliance of FIGS. 6-7, looking toward its lingual side.

FIG. 7A shows that the first and second protrusions 236a, 236b need not be identical. For example, it can be advantageous for the first protrusion 236a to have a triangular cross-section, as viewed from the lingual direction. For example, orienting the first protrusion 236a such that a vertex of the triangle points toward the entrance to the recess 222 can reduce the force required to assemble the door 210 to the body 204. As an added benefit, once the clip 220 has been assembled to the body 204, a side surface of the triangular first protrusion 236a can flatly engage the gingival-facing surface of the clip 220 to prevent accidental disassembly of the door 210. The first protrusion 236a can thus have a shape allowing easy passage through the clip 220 in the gingival direction but not the occlusal direction. By constrast, the second protrusion 236b has a substantially round cross-section to enable reversible passage of the second protrusion 236b through the clip 220 in gingival and occlusal directions.

Once again, the process of opening and closing the door 210 can be made reversible because of the resilient nature of the clip 220. As the treating professional imparts occlusal and gingival forces to open and close the door 210, the mesial and distal sections 252, 254 elastically spread in directions away from each other, thereby allowing the second protrusion 236b to toggle between residing in the first and second regions 238, 240, respectively.

Figure 9:
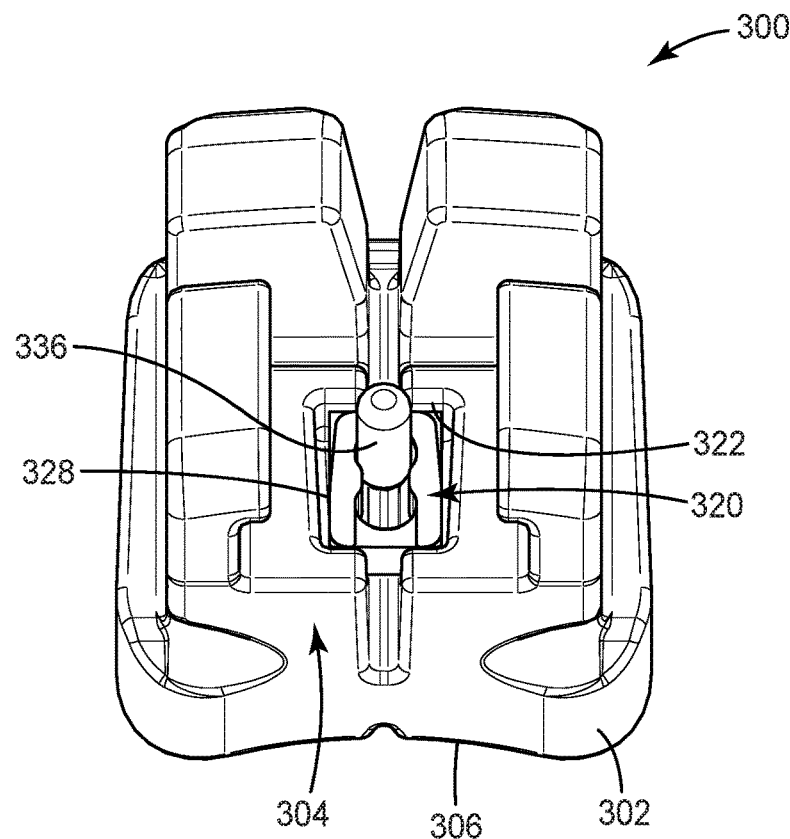
FIG. 9 is a perspective view of an orthodontic appliance according to another embodiment, with a component omitted to show hidden features of the appliance, looking toward its occlusal and facial sides.
Figure 10:
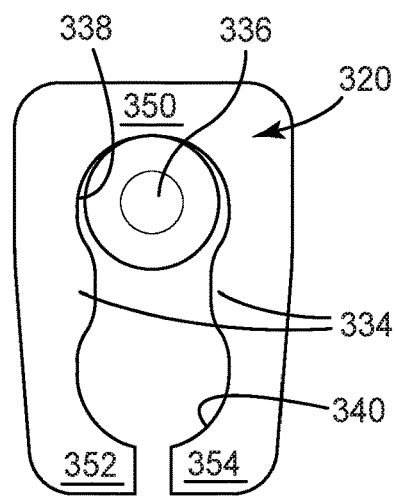
FIG. 10 is an enlarged fragmentary plan view showing the mechanical interaction between two components of the appliance of FIG. 9.

FIG. 9 shows another appliance 300 with its door (hidden in FIGS. 9-10 for clarity). Like previous appliances, the appliance 300 has a base 302 having an underlying bonding surface 306, body 304, and recess 322 on the outward facing side of the body 304. Received in the recess 322, however, is a resilient planar clip 320 having a generally "U"-shaped configuration. A protrusion 336 is also received in the recess 322, and can be integral with the door, or a discrete component partially embedded in the door as previously described and shown in the appliance 100 of FIG. 4A.

FIG. 10 shows the interaction between the protrusion 336 and the clip 320 in more detail. As shown, the clip 320 has a center section 350 and a pair of arm sections 352, 354. The arm sections 352, 354 include respective inward-facing projections 334 that divide the space enclosed by the sections 350, 352, 354 of the clip 320 into gingival and occlusal regions 338, 340. In FIGS. 9 and 10, the protrusion 336 resides in an equilibrium position within the gingival region 338, corresponding to the closed position of the door. When there is sufficient applied force urging the door toward a generally occlusal direction, the associated protrusion 336 causes the arm sections 352, 354 to elastically deflect in respective mesial and distal directions, allowing the protrusion 336 to slide past the opposing projections 334 until it fully resides in another equilibrium position within the occlusal region 340, corresponding to the opened position of the door. Being resilient, the arm sections 352, 354 can return toward their original relaxed states and retain the protrusion 336 in the region 340.

Referring again to FIG. 9, the deflection of clip 320 occurs along a reference plane that is generally coplanar with the clip 320 itself. This reference plane is also parallel to both a bottom wall 328 of the recess 322 and an underlying bonding surface 306 of the base 302. Advantageously, such a configuration can help decrease the facial-lingual profile of the appliance, because the recess 322 and the clip 320 therein can be made relatively thin. The ease by which the protrusion 336 slides between the regions 338, 340 can be adjusted based on the cross-sectional dimensions of the sections 350, 352, 354 and the size and shape of the inwardly-facing projections 334. The mechanism whereby the clip 320 engages and disengages with the protrusion 336 is optionally similar to the mechanisms described in U.S. Pat. No. 6,302,688 (Jordan et al.) and U.S. Pat. No. 6,582,226 (Jordan et al.), except the clip 320 here engages a sliding door rather than an archwire.

It is to be understood that many other aspects of appliance 300 may have similar form and function to those described in appliances 100, 200 and these will not be repeated.

Optionally, any of the appliances 100, 200, 300 could use a clip 120, 220, 320 that exerts a continuous force on the protrusion 136, 236a, 236b, 336. Preferably, this force is a compressive force, resulting from the clip 120, 220, 320 being maintained in a partially stressed (i.e. unrelaxed) state. This can be achieved by using a protrusion that is over-sized. For example, the cross-sectional diameter of the protrusion 136, 236a, 236b, 336 could be made intentionally larger than at least some of the regions 138, 140, 238, 240, 338, 340. This feature can provide a snug fit between the door 110, 210 and the body 104, 204, 304 and preventing the door 110, 210 from rattling while engaged to the body 104, 204, 304.

Having a clip that exerts a continuous force on the protrusion can be of particular benefit when dealing with appliances in which there are significant gaps between the door and the body. As mentioned previously, gaps are sometimes desirable to facilitate sliding of the door and avoid binding. Additionally, such gaps can also help provide sufficient space on the mesial and distal sides of the door to allow for mesial-distal debonding of the appliance from the tooth at the end of treatment. In some embodiments, the assembled door and body have a pre-determined cumulative mesial-distal gap width of at least about 25 micrometers (1 mil), at least about 38 micrometers (1.5 mils), or at least about 51 micrometers (2 mils); in some embodiments, the gap width is up to about 130 micrometers (5 mils), up to about 100 micrometers (4 mils), or up to about 76 micrometers (3 mils).

Figure 11:
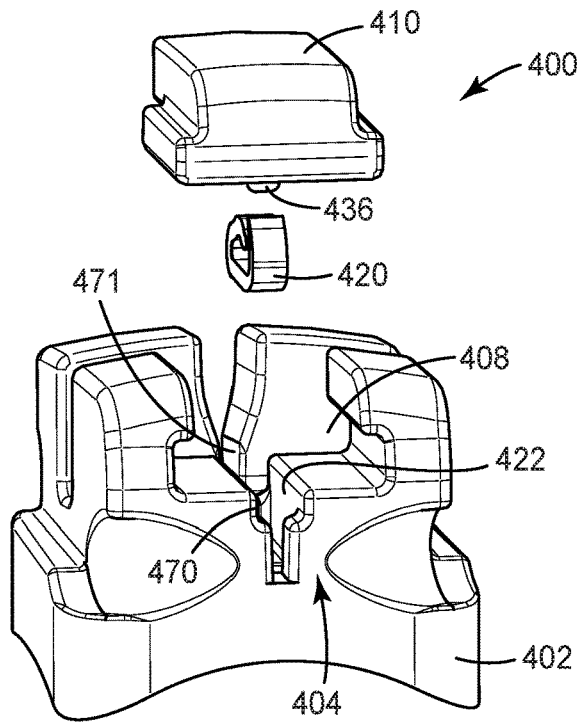
FIG. 11 is an exploded perspective view of an orthodontic appliance according to another embodiment, looking toward its occlusal, mesial, and facial sides.
Figure 12:
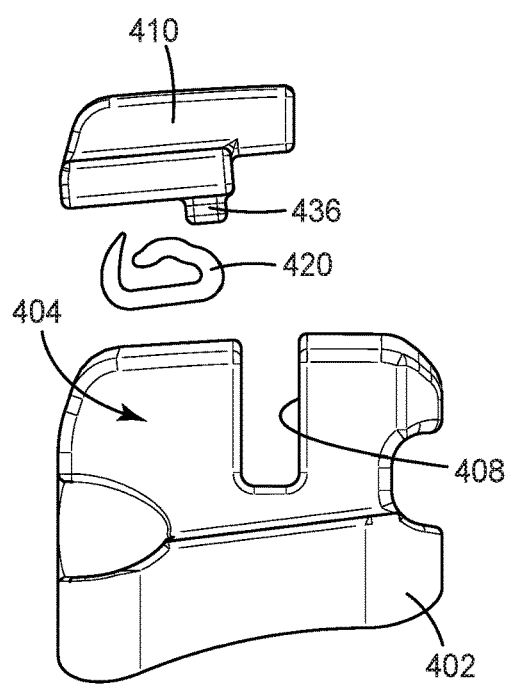
FIG. 12 is an exploded side elevational view of the appliance of FIG. 11, looking toward its mesial side.

FIGS. 11 and 12 are exploded views showing an appliance 400 according to another embodiment. The appliance 400 has many features in common with those already described, including a base 402, a body 404 joined to the base 402, and an archwire slot 408 extending across the body 404. The appliance 400 further includes a door 410 slidably received in the body 404 and having an integral protrusion 436. The body 404 has a recess 422 adjacent the slot 408 that receives a clip 420.

Figure 13A:
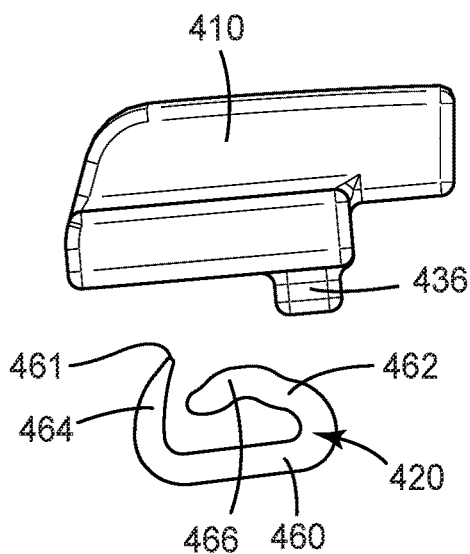
FIG. 13A is an exploded side elevational view of two components of the appliance of FIGS. 11-12, looking toward their mesial sides.

As shown alongside the door 410 in FIG. 13A, the exemplary clip 420 has an asymmetric configuration when viewed from the mesial or distal direction. The clip 420 is planar and resides in a reference plane generally perpendicular to the mesial-distal axis of the appliance 400. Further, the clip 420 includes a center section 460, an arched section 462, and a tail section 464. The center section 460 is approximately linear and extends adjacent and parallel to a bottom wall 428 of the recess 422. In a preferred embodiment, the center section 460 flatly engages the bottom wall 428 and does not significantly move relative to the recess 422 during normal operation of the door 410.

The arched section 462 of the clip 420 is joined to the gingival end of the center section 460 and extends toward the occlusal direction, whereby the arched section 462 forms a generally "U" shaped configuration with respect to the center section 460. The arched section 462 has an arch 466 that is located near the geometric midpoint between the occlusal and gingival edges of the clip 420. This exemplary arch 466 is characterized by a convexity on the facial surface of the arched section 462, and the arch 466 faces a generally facial direction when received in the recess 422 of the body 404. As shown in FIGS. 6-8, the arch 466 and protrusion 436 oppose each other when the appliance 400 is assembled.

The tail section 464 of the clip 420 is joined to the occlusal end of the center section 460 and extends in a generally facial-gingival direction such that the tail section 464 forms an acute angle α (shown in FIG. 13B) relative to the center section 460 when relaxed. In some embodiments, the angle α formed between the tail section 464 and the center section 460 is at least about 45 degrees, at least about 50 degrees, or at least about 70 degrees when the clip 420 is relaxed. In some embodiments, the angle formed between the tail section 464 and the center section 460 is up to about 90 degrees, up to about 85 degrees, or up to about 75 degrees when the clip 420 is relaxed.

Optionally and as shown, the tail section 464 has a cross-sectional dimension that varies along its length. In this embodiment, the tail section 464 has a cross-sectional dimension that monotonically decreases with increasing distance from the center section 460, and is thinnest at its terminal end 461. Tapering the tail section 464 in this manner increases the overall flexibility of the section 464 relative to the remaining sections 460, 462. This can provide certain functional advantages for the clip 420, as will be discussed in the following sections.

Figure 13B:
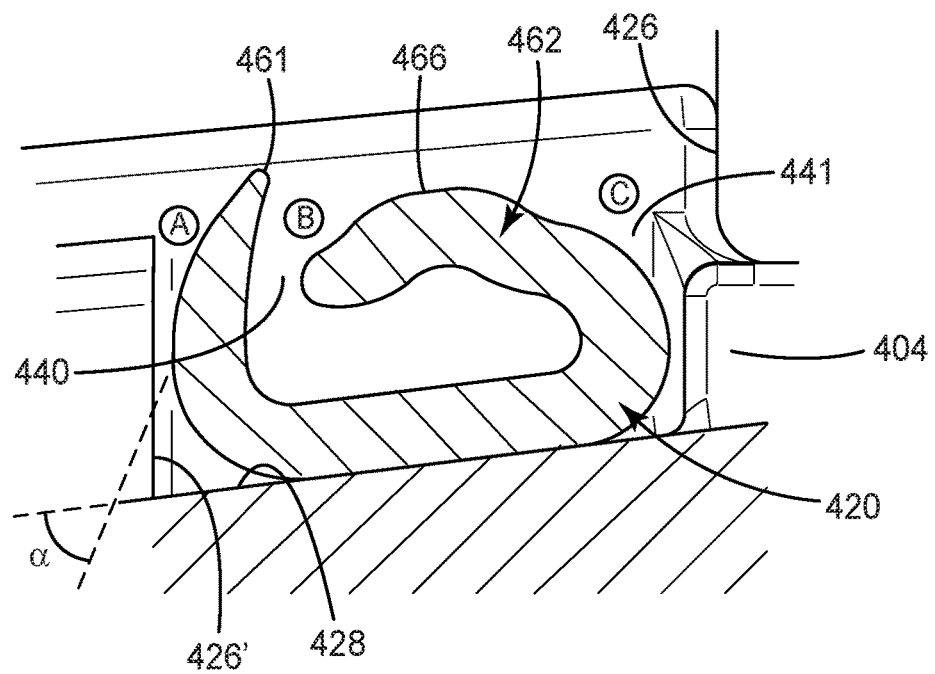
FIG. 13B is a fragmentary cross-sectional view of the appliance of FIGS. 11-13A, looking toward a mesial-facing cross-sectional surface.

Referring now to FIG. 13B, the terminal end 461, arch 466, and gingival side wall 426 (of the recess 422) are linearly spaced apart from each other along an occlusal-gingival axis and collectively define certain regions where the protrusion 436 may reside. When located in the position labeled "A," the protrusion 436 is on the occlusal side of the terminal end 461, arch 466, and gingival side wall 426. In this position, the door 410 is still disassembled from the body 404 and can freely slide in the occlusal direction along an enlarged opening 470 located on the occlusal side wall of the recess 422 (shown in FIG. 11). Because the opening 470 is wider than the protrusion 436 along the mesial-distal direction, the door 410 can continue sliding in the occlusal direction until the door 410 is dislodged from the body 404.

When sufficient force is applied to the door 410 in a generally gingival direction, the protrusion 436 presses against the terminal end 461, causing it to deflect downwards (i.e. in a lingual direction) and permit the protrusion 436 to "snap" into the position labeled "B." In this position, the protrusion 436 is now on the gingival side of the terminal end 461 and the occlusal side of the arch 466 and the gingival side wall 426. Here, the protrusion 436 is constrained in an equilibrium position between the terminal end 461 and the arch 466, which collectively define an occlusal region 440. The appliance 400 is now in assembled form, with the door 410 in its opened position.

From this configuration, additional force can be applied to the door 410 in a gingival direction to close the door 410. Upon reaching a threshold amount of force, the arched section 462 resiliently "flattens" to allow passage of the protrusion 436 into its third position, labeled "C" in FIG. 13B. In this position, the protrusion is located on the gingival side of both the terminal end 461 and arch 466 but on the occlusal side of the gingival side wall 426. Here, the protrusion 436 is constrained in a second equilibrium position between the arch 466 and the gingival side wall 426, which collectively define a gingival region 441. With the protrusion 436 now in the gingival region 441, the door 410 is closed. The arched section 462 springs back toward its original position to retain the protrusion 436 and prevent the door 410 from spontaneously opening. While there is an opening 471 on the gingival side wall 426 that divides the appliance 400 to facilitate debonding, the mesial-distal width of the opening 471 is less than that of the protrusion 436, thus preventing further gingival movement of the door 410.

In at least some embodiments, the tail section 464 acts as a pawl that facilitates assembly of the door 410 to the body 404 while preventing accidental disassembly. This advantage is enabled by the orientation of the tail section 464, which is slanted toward a slightly gingival direction as shown, for example, in FIG. 13A. When the protrusion 436 presses against the tail section 464, there is sufficient clearance on the gingival side of the tail section 464 for it to resiliently bend toward the center section 460 and permit passage of the protrusion 436 over the tail section 464 and into region "B" within the recess 422. Once the protrusion 436 has entered region "B," however, it cannot then easily escape from the recess 422 because of the gingival slant in the tail section 464. Moreover, the occlusal side wall 426' of the recess 422 constrains the tail section 464 from deflecting significantly in the occlusal direction. As a result of these features, the assembly of the door 410 to the body 404 can be made substantially irreversible.

Figure 14:
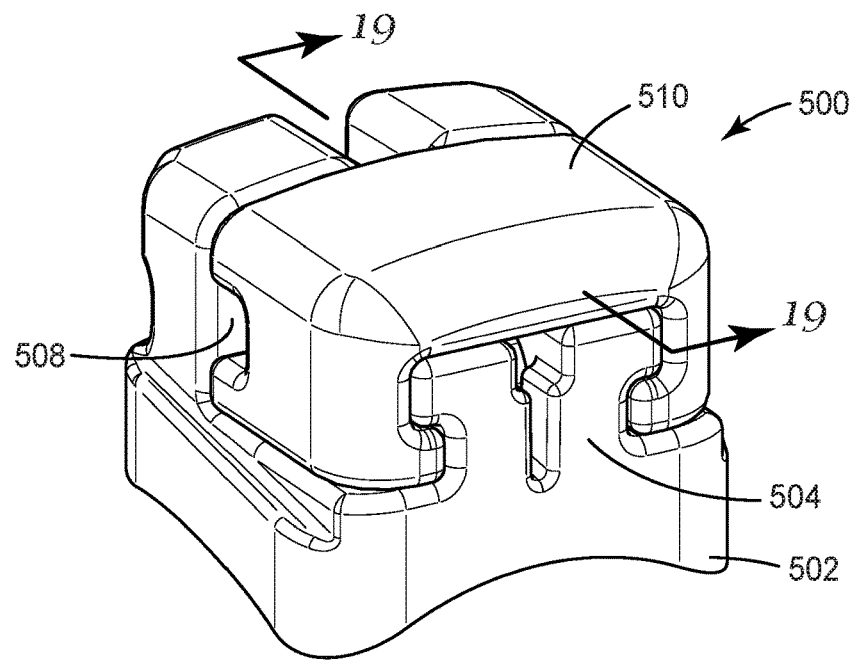
FIG. 14 is a perspective view of an orthodontic appliance according to another embodiment, looking toward its occlusal, mesial, and facial sides.
Figure 15:
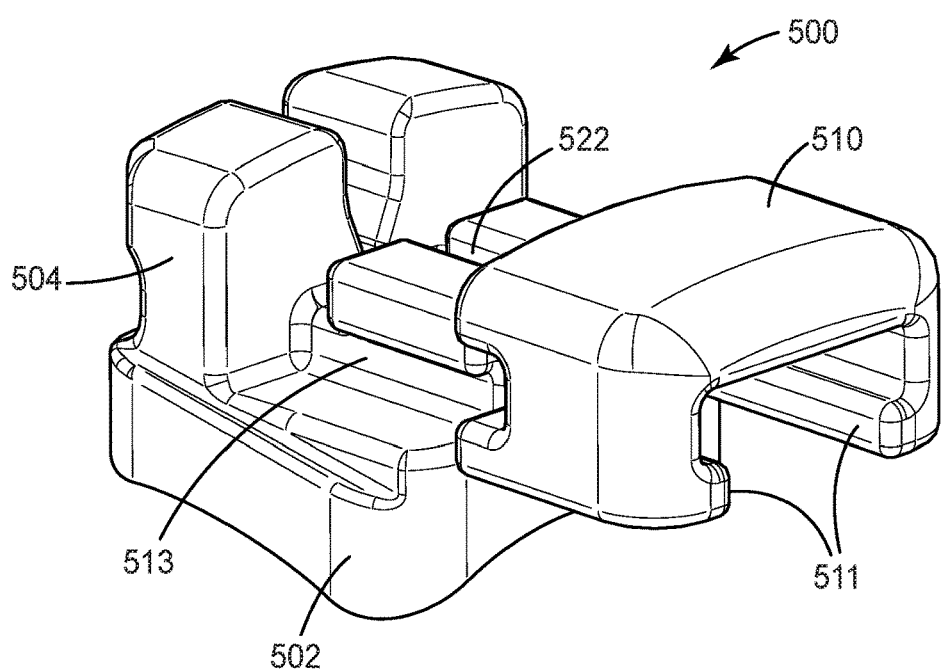
FIG. 15 is a perspective view of the appliance of FIG. 14 in a disassembled configuration, looking toward its occlusal, mesial, and facial sides.

FIGS. 14-19 illustrate an appliance 500 according to another embodiment similar in many respects to those shown in FIGS. 11-13B, but with additional options and advantages. As shown in FIGS. 14 and 15, the appliance 500 has a base 502, a body 504 extending from the base 502, and an archwire slot 508 extending across the body 504 in a generally mesial-distal direction. The appliance 500 further includes a door 510 that is slidably engaged to the body 504 and toggles between a slot open position where the slot 508 is accessible and a slot closed position where the slot 508 is not accessible.

The door 510 is a "wide door" differing from those previously shown because it has a mesial-distal width that substantially matches the overall mesial-distal width of the overall appliance 500. Advantageously, this feature can provide enhanced rotational control during orthodontic treatment (affecting rotational movement of the tooth about its long axis), since it increases the distance along which an archwire can engage, and apply therapeutic forces to, the door 510 of the appliance 500. Here, the door 510 has inward-facing rails 511 protruding in mesial and distal directions and longitudinally extending across the door 510 in a generally occlusal-gingival direction. As shown, the rails 511 are received in complementary grooves 513 located on mesial-facing and distal-facing surfaces of the body 504. Together, the rails 511 and grooves 513 guide the operative sliding motion of the door 510.

Figure 16:
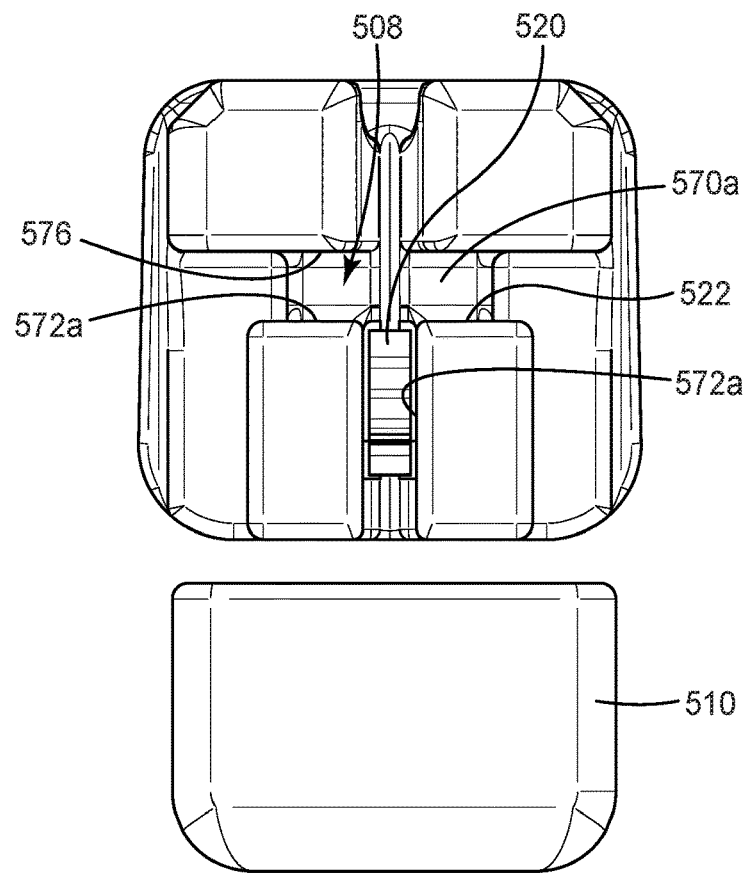
FIG. 16 is a plan view of the appliance of FIGS. 14-15 in a disassembled configuration, looking toward its facial side.

Referring to FIG. 16, the body 504 also has an elongated recess 522 that is located adjacent the slot 508 and receives an integral, resilient clip 520. Similar to the clip 420 in appliance 400, the clip 520 is substantially coplanar with a reference plane perpendicular to the mesial-distal longitudinal axis of the slot 508 and generally bisecting the appliance 500 into mesial and distal halves. Referring now to the cross-sectional view of FIG. 19, the clip 520 is held captive in the recess 522 by occlusal and gingival walls 526, bottom wall 528, and the door 510.

Figure 17:
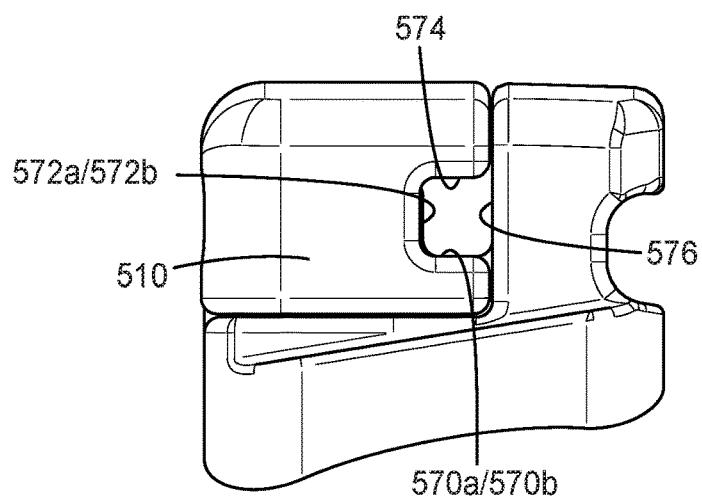
FIG. 17 is a distal view of the appliance of FIGS. 14-16 in a slot closed position, looking toward its distal side.
Figure 18:
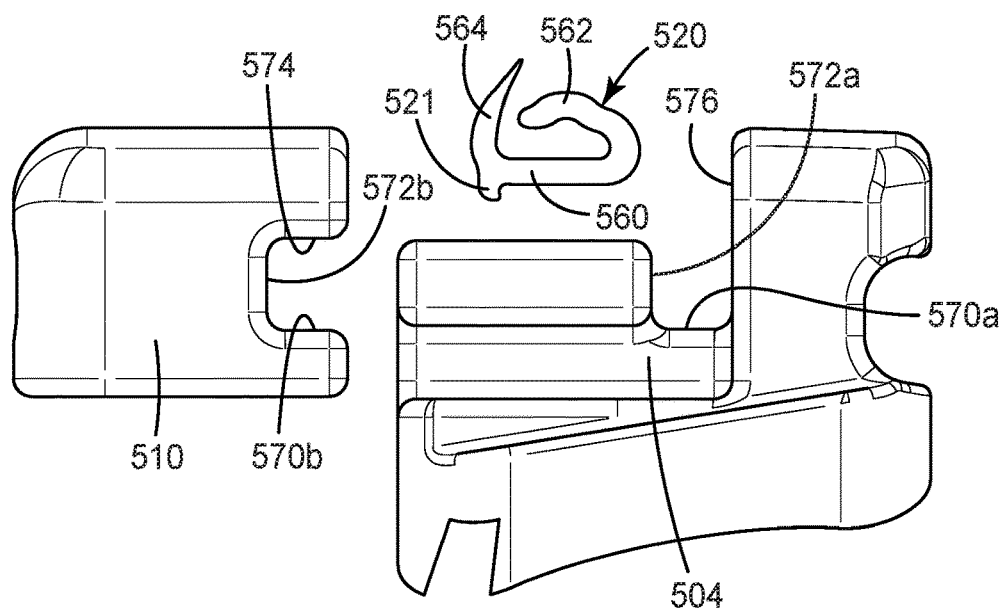
FIG. 18 is an exploded side elevational view of the appliance of FIGS. 14-17, looking toward its distal side.

When the door 510 is in its closed position, the slot 508 is enclosed by four substantially rigid walls. Optionally and as shown in FIGS. 17-18, the slot 508 has a bottom wall that is collectively defined by both a partial bottom wall 570a located on the body 504 and a pair of partial bottom walls 570b located on the door 510. The partial bottom walls 570b extend along mesial and distal portions of the slot 508, and straddle the partial bottom wall 570a, which extends along a central portion of the slot 508. Similarly, the slot 508 includes an occlusal wall collectively defined by a partial occlusal wall 572a on the body 504 and a pair of partial occlusal walls 572b on the door 510 that straddle the partial occlusal wall 572a. In this particular embodiment, the slot 508 has a facial wall 574 defined exclusively by the door 510 and a gingival wall 576 exclusively defined by the body 504.

One benefit of the configuration described above is the lengthened interface between the rails 511 and respective grooves 513. More specifically, this mechanism allows the rails 511 and groove 513 to effectively traverse not only the gingival half of the appliance 500 but also the occlusal-gingival width of the slot 508. By increasing the occlusal-gingival length along which these mating surfaces engage each other, this configuration enhances stability, and reduced wobbling, of the door 510 as it slides open and closed along the body 504. This is especially useful where the appliance 500 is made as small as possible for patient comfort and space on the body 504 is limited.

Figure 19:
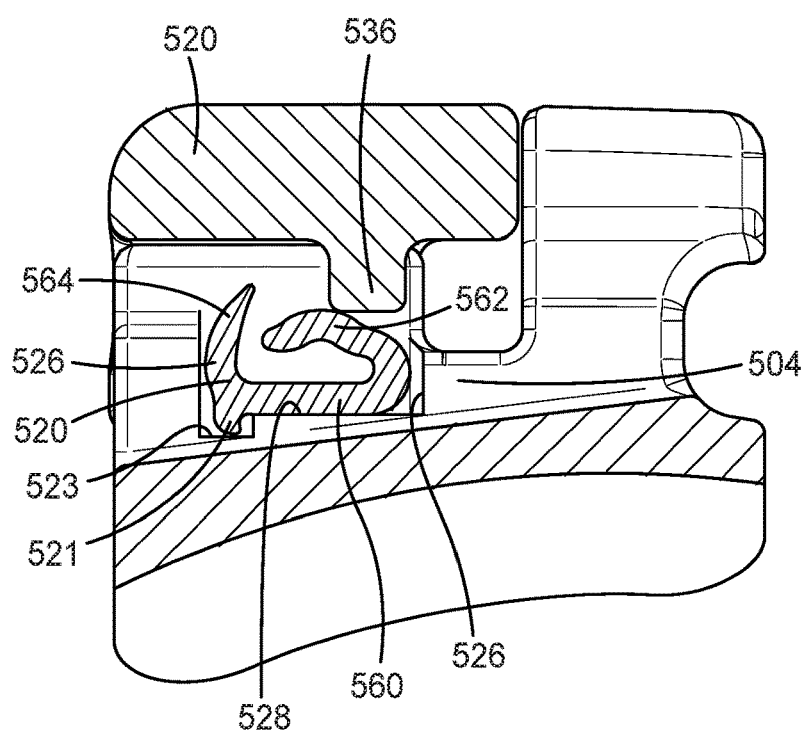
FIG. 19 is a cross-sectional side elevational view of the appliance of FIGS. 14-18 along the section 19-19 in FIG. 14 and looking toward a distal-facing cross-sectional surface.

The clip 520, including a center section 560, an arched section 562, and tail section 564, has substantially the same form and function as the clip 420 of appliance 400. Optionally and as shown in FIGS. 18 and 19, however, the clip 520 includes an extended corner portion 521 located between the center section 560 and tail section 564 that protrudes in a lingual direction toward the bottom wall 528 of the recess 522. The bottom wall 528 of the body 504 also includes a cavity 523 that precisely registers with and receives the corner portion 521 when the clip 520 is seated in the recess 522. As shown in FIG. 19, the cavity 523 advantageously anchors the clip 520 to the body 504, creating a reaction force that prevents the clip 520 from rotating, even when excessive opening forces are applied to the door 510.

The presence of the corner portion 521 can provide a more robust appliance 500 in view of both operator misuse and manufacturing variability. For example, if a treating professional forcefully attempts to slide the door 510 in the occlusal direction even after the door 510 is fully open, the corner portion 521 contacts the gingival (i.e. occlusal-facing) wall of the cavity 523. The gingival wall of the cavity 523 thus acts as a positive stop that keeps the clip 520 from toppling counterclockwise out of the recess 522. Since the clip 520 is restrained from rotation, overextension of the door 510 is prevented as the tail section 564 interferes with further occlusal movement by a protrusion 536 on the door 510. This independent interaction between the corner portion 521 and cavity 523, while not essential, helps increase tolerance for small gaps that may be present between the door 510 and body 504, variability in the shape of the clip 520, and other minor manufacturing irregularities.

Other aspects of the appliances 400, 500 are analogous to those previously described and do not need repeating for the skilled person.

Figure 20:
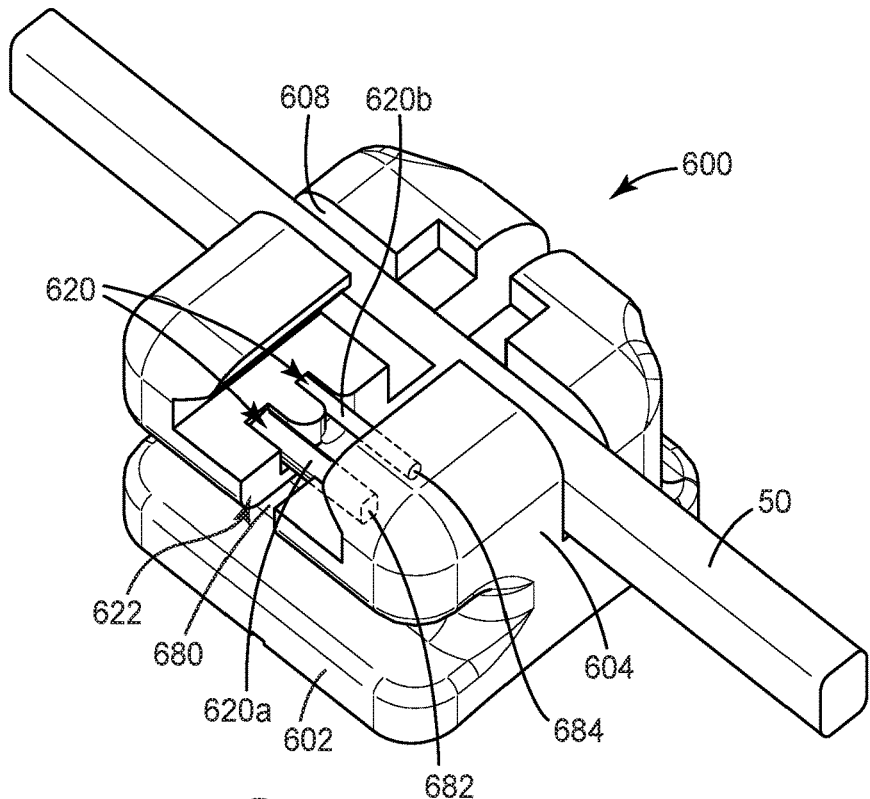
FIG. 20 is a perspective view of an orthodontic appliance according to another embodiment, with one component omitted to show hidden features of the appliance, looking toward its facial, distal, and occlusal sides.

FIGS. 20-25 illustrate another exemplary embodiment that uses a non-unitary retention member (i.e. one including at least two discrete components). FIG. 20 shows a partial appliance 600 having a base 602, a body 604, and archwire slot 608. The body 604 has a compound recess 622 that includes a central channel 680 extending in a generally occlusal-gingival direction and closed-ended lateral channels 682, 684, each extending in a generally mesial-distal direction across the central channel 680. The appliance 600 uses a clip 620 having a rectangular beam 620a and round beam 620b held captive within respective lateral channels 682, 684. The appliance 600 also includes an integral door 610 shown in FIG. 21. The door 610 has a protrusion 636 that is in registration with the central channel 680 when the door 610 is assembled to the body 604. The door 610 has rails enabling it to slide in occlusal and gingival directions along substantially matching grooves located on the body 604.

Figure 23:
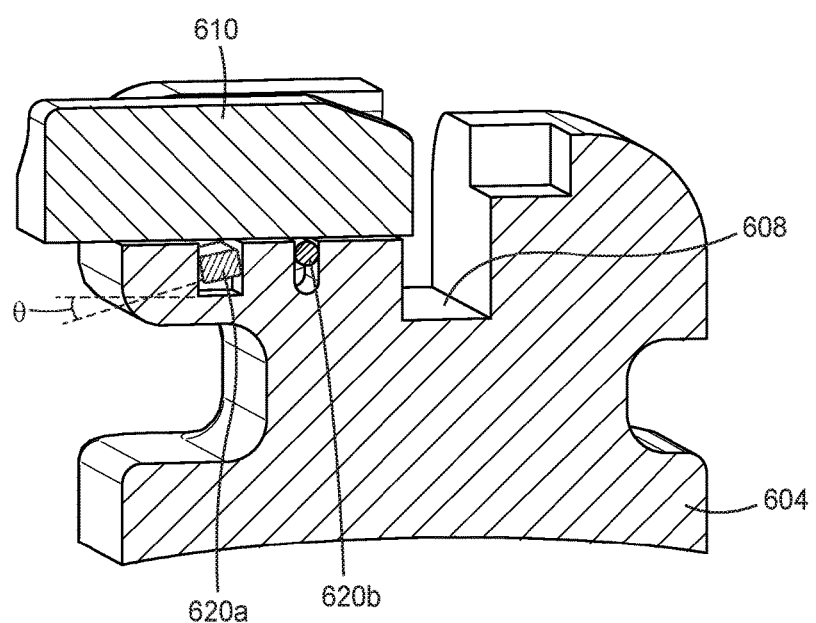
FIG. 23 is a perspective cross-sectional view of the appliance of FIG. 20, looking toward a distal-facing cross-sectional surface.

The rectangular beam 620a is adjacent the occlusal entrance to the recess 622. The round beam 620b, on the other hand, is remote from the occlusal entrance to the recess 622, being spaced from the beam 620a toward the gingival direction. As further shown in the cross-sectional view of FIG. 23, the long cross-sectional dimension (width) of the rectangular beam 620a extends along an axis oriented at a slight acute angle θ relative to the sliding direction the door 610. In some embodiments, the angle θ is at least about 0.1 degrees, at least about 0.5 degrees, or at least about 1 degree. In some embodiment, the angle θ extends up to about 90 degrees, up to about 45 degrees, or up to about 10 degrees. Optionally and as shown in FIG. 23, the angle θ can be built into the bottom surface of the lateral channel 682 in which the beam 620a resides.

Figure 24:
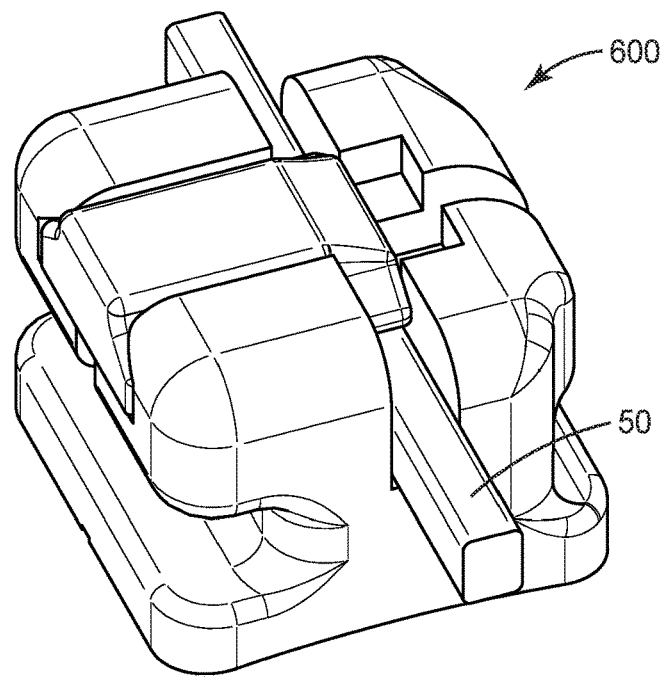
FIG. 24 is a perspective view of the appliance of FIGS. 20 and 23 engaging an archwire in a slot closed position, looking toward its facial, distal, and occlusal sides.
Figure 25:
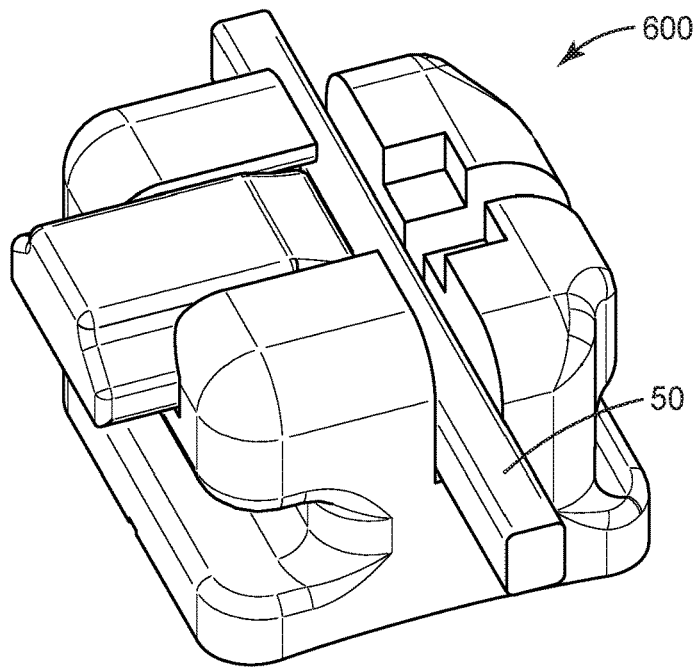
FIG. 25 is a perspective view of the appliance of FIGS. 20, 23, and 24, engaging an archwire in a slot open position, looking toward its facial, distal, and occlusal sides.

By virtue of this relative arrangement of the beams 620a, 620b, the protrusion 636 first traverses the rectangular beam 620a, then traverses the round beam 620b as it is slidably assembled to the body 604. In the assembly of the door 610, each beam 620a, 620b independently functions as a latch by resiliently deflecting toward the bottom surface of the recess 622 to permit passage of the protrusion 636 as the associated door 610 is urged in a gingival direction against the beam 620a, 620b. As the protrusion 636 slides toward an equilibrium position on the opposite side of the beam 620a, 620b, the beam 620a, 620b flexibly returns toward its original shape, thereby preventing the door 610 from easily sliding back across the beam 620a, 620b. The door 610 can be reversibly opened and closed, as shown in FIGS. 24 and 25, by sliding the protrusion 636 back and forth between regions on the occlusal and gingival sides of the round beam 620b.

Figure 22:
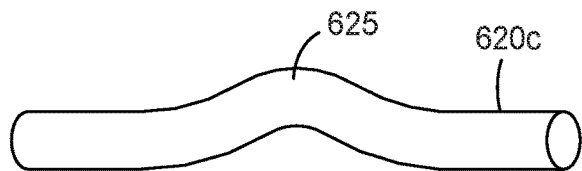
FIG. 22 is an enlarged perspective view of a particular component of the appliance of FIG. 20.

Optionally, one or both beams 620a, 620b could have a curved configuration along some or all of its length. For example, FIG. 22 shows a beam 620c is provided with a dimple 625 approximately located at the midpoint of the beam 620c. The dimple 625 provided in one or both beams 620a, 620b can increase the clearance required for the protrusion 636 to pass over the beams 620a, 620b and accommodate manufacturing tolerances in the height of protrusion 636 and the mating surfaces between the door 610 and the body 604.

The rectangular beam 620a has a geometry and orientation that facilitates the assembly of the door 610 to the body 604, while also preventing spontaneous or inadvertent separation of the door 610 from the body 604 when a treating professional normally opens and closes the door 610. FIG. 23 shows the door 610 located in a region of the recess 622 between the rectangular and round beams 620a, 620b. In this figure, the door 610 is subjected to a force vector in the occlusal (opening) direction. Because of the slight tilt in the beam 620a, a gingival-facing surface of the beam 620a flatly engages an occlusal-facing surface of the protrusion 636. The gingival-facing surface of the beam 620a therefore acts as a positive stop that impedes passage of the protrusion 636 over the beam 620a in the occlusal direction. As a further benefit, the tilt in the beam 620a also acts as a ramp that assists with the initial assembly of the door 610 in the body 604.

Figure 21:
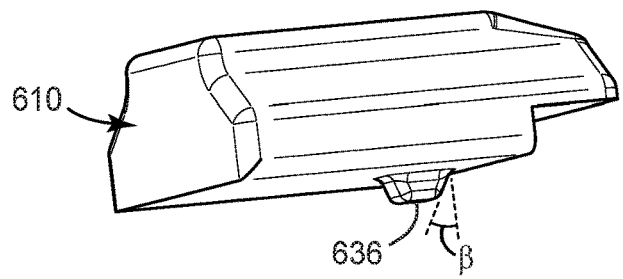
FIG. 21 is an enlarged perspective view of the component omitted in FIG. 20, looking toward its occlusal, mesial, and lingual sides.

In some embodiments, the geometry of the protrusion 636 can also be tailored to adjust the forces required to open and close the door 610. As shown in FIG. 21, for example, the opening and closing forces can be generally decreased by using a protrusion 636 having a generally trapezoidal profile (as viewed from the mesial or distal direction) and having a suitable side wall angle β. In some embodiments, the side wall angle β is less than about 45 degrees, less than about 35 degrees, or less than about 30 degrees. Conversely, the opening and closing forces can be increased by using a side wall angle β greater than about 45 degrees, greater than about 55 degrees, or greater than about 60 degrees. If desired, asymmetric opening and closing forces can be realized by using a trapezoidal protrusion 636 with substantially different side wall angles (e.g. $\beta_1$ and $\beta_2$). For example, the leading (or gingival-facing) edge of the protrusion 636 could have a side wall angle of 40 degrees, while the trailing (or occlusal-facing) edge of the protrusion 636 could have a side wall angle of 60 degrees. Such a configuration allows threshold opening forces to be intentionally increased, preventing the door 610 from accidently opening during mastication.

The forces of opening and closing the doors are determined by the material properties, protrusion dimensions and the cross-sectional dimensions of the beams 620a, 620b. Preferably, the beams 620a, 620b are short wire segments of a superelastic nickel-titanium alloy. In one exemplary embodiment, the round beam 620b has a diameter of 0.20 millimeters (0.008 inches) while the rectangular beam 620a has "A" and "B" dimensions of 0.15 millimeters and 0.25 millimeters (0.006 inches and 0.010 inches), respectively. In this embodiment, the beams are 1.22 millimeters (0.048 inches) long. The protrusion 636 has a height of 0.20 millimeters (0.008 inches) and an area of 0.356 millimeters× 0.25 millimeters (0.014 inches×0.010 inches). The clearance between the door 610 and the body 604 is about 19 micrometers (0.00075 inches) on all surfaces.

Figure 26:
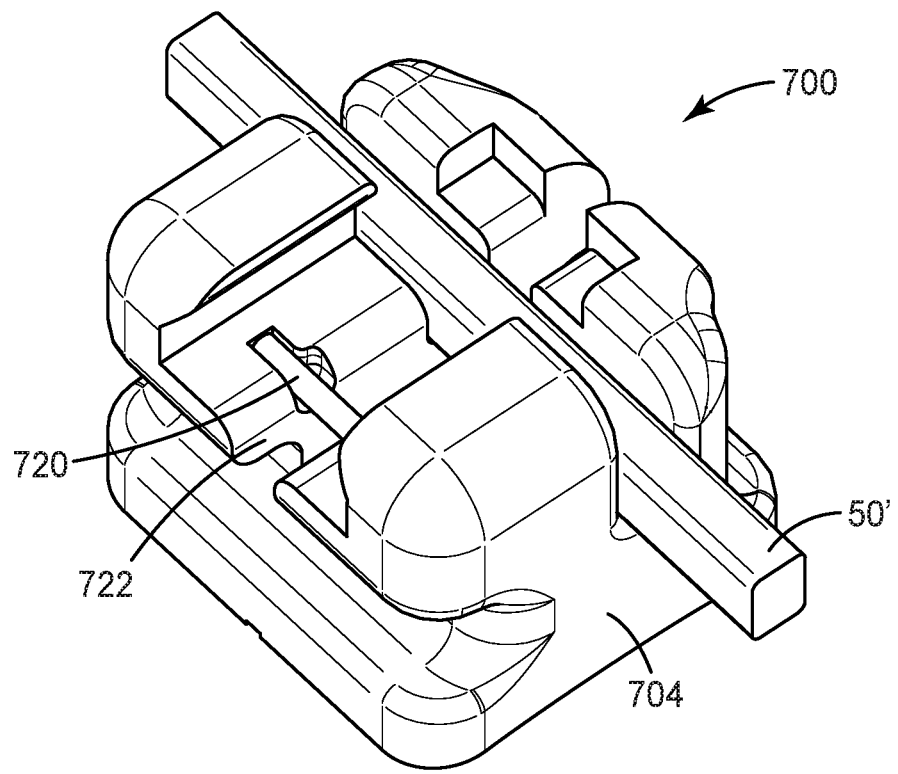
FIG. 26 is a perspective view of an orthodontic appliance engaging an archwire according to another embodiment, with a component omitted to show hidden features of the appliance, looking toward its facial, distal, and occlusal sides.
Figure 27:
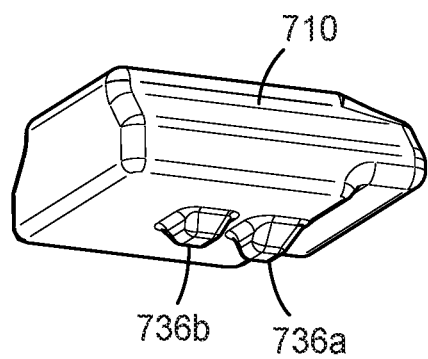
FIG. 27 is an enlarged perspective view of the component omitted from FIG. 26, looking toward its distal, occlusal, and lingual sides.

Still another embodiment is provided by the appliance 700 engaging exemplary archwire 50', as illustrated in FIGS. 26 and 27. The appliance 700 is essentially the same as the appliance 600 in most respects, but uses a unitary clip 720 residing in a recess 722 of a body 704, and a door 710 with gingival and occlusal protrusions 736a and 736b. The protrusions 736a, 736b engage the clip 720 as the door 710 is assembled to the body 704. Here, the protrusion 736b toggles between regions on the gingival and occlusal sides of the clip 720, corresponding to closed and open door configurations, respectively. The protrusion 736a is provided with an asymmetric trapezoidal configuration to prevent accidental disassembly of the door 710 from the body 704 in normal operation.

The appliance doors embodied above preferably have force characteristics that enable the treating professional to easily open and close the door using a common orthodontic hand instrument, such as an orthodontic explorer. Optionally, a specialized hand instrument could be used to limit the sliding motion of the door; for example, a flat probe could be inserted in the seam between the leading edge of the door and the body, and then twisted to open the door. This could help reduce the risk of accidental debonding. In some embodiments, the threshold force used to open the door is at least about 50 gram-force, at least about 200 gram-force, or at least about 500 gram-force. In some embodiments, the threshold force used to open the door is up to about 5000 gram-force, up to about 3000 gram-force, or up to about 1000 gram-force.

Figure 28:
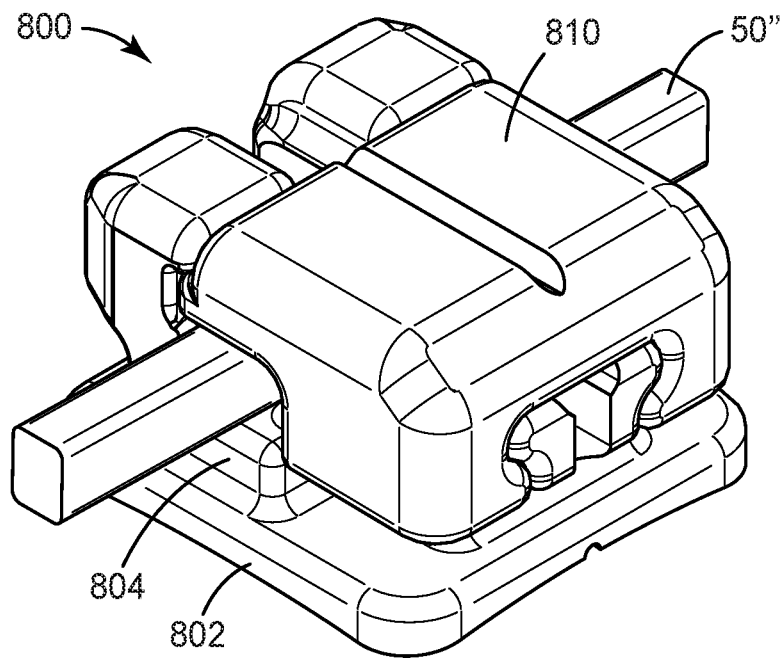
FIG. 28 is a perspective view of an orthodontic appliance according to another embodiment, looking toward its facial, mesial, and occlusal sides.
Figure 29:
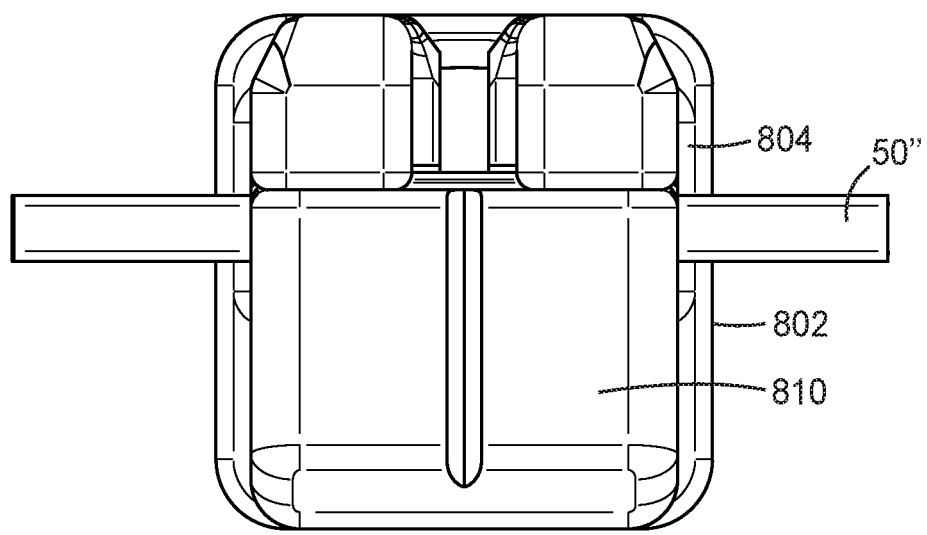
FIG. 29 is a facial view of the appliance of FIG. 28, looking toward its facial side.
Figure 30:
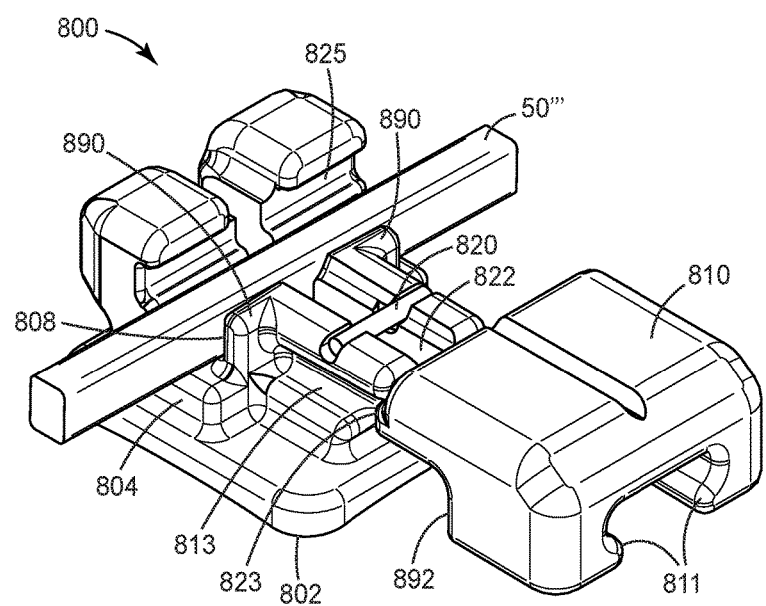
FIG. 30 is an exploded perspective view of the appliance of FIG. 28-29, looking toward its facial, mesial, and occlusal sides.

FIGS. 28-30 show an appliance 800 engaging an exemplary archwire 50" in yet another embodiment, the appliance 800 having a base 802, a body 804, and a door 810. Like in appliance 500 previously described, the door 810 has a pair of inwardly protruding rails 811 that slide along a pair of grooves 813 located on respective mesial-facing and distal-facing sides of the body 804. As shown in FIG. 30, the door 810 passes over a generally cross-shaped recess 822 retaining a resilient clip 820 having a mode of operation similar to that of clip 720, where a protrusion (not visible) extending in a lingual direction from the door 810 causes the clip 820 to resiliently deflect when toggling the door 810 between opened and closed positions and a second protrusion (not visible) extending in a lingual direction from the door 810 prevents the door 810 from falling out when the door 810 is in an open position.

Optionally, the door 810 has an overall mesial-distal width that is slightly smaller than the mesial-distal width of the body 804 to facilitate squeeze-debonding the appliance 800. In the process of squeeze-debonding, compressive forces provided by a hand instrument will be concentrated on the body 804 rather than the door 810, enabling the appliance to collapse properly. The difference in the mesial-distal dimension between the door 810 and body 804 can range, for example, from about 0.051 millimeters (0.002 inches) to about 0.254 millimeters (0.010 inches).

Referring again to FIG. 30, the appliance 800 differs from previous appliances in that it includes a pair of rigid integral walls 890 that partially define an archwire slot 808 for accommodating the archwire 50'''. The integral walls 890 are located gingival and adjacent to the recess 822 and define a majority of the gingival wall of the archwire slot 808. The remaining portions of the gingival wall of the archwire slot 808 are provided by a pair of gingival-facing surfaces 892 of the door 810, as shown. The gingival-facing surfaces 892 are located adjacent the mesial and distal sides of the appliance 800. Advantageously, the integral walls 890 can provide for more secure ligation by allowing the archwire 50''' to impart substantial torque (i.e. twisting forces) to the appliance 800 without undesirably opening the door 810.

In some embodiments, the integral walls 890 extend along at least about 40 percent, at least about 45 percent, at least about 50 percent, at least about 55 percent, or at least about 60 percent of the archwire slot 808. In some embodiments, the integral walls 890 extend along at most about 90 percent, at most about 85 percent, at most about 80 percent, at most about 75 percent, or at most about 70 percent of the archwire slot 808.

As further shown in FIG. 30, the leading edge 823 of door 810 engages a complementary recess 825 next to the gingival wall of the archwire slot 808 as the door 810 is slidably moved into its closed position. Engagement of the convex leading edge 823 with the mating complementary recess 825 helps limit undesirable movement of the door 810 that can result from the clearance between the door 810 and body 804 when the appliance 800 is subjected to rotation relative to the occlusal-gingival axis or labial movement in the labial direction of the archwire 50'''.

Figure 31:
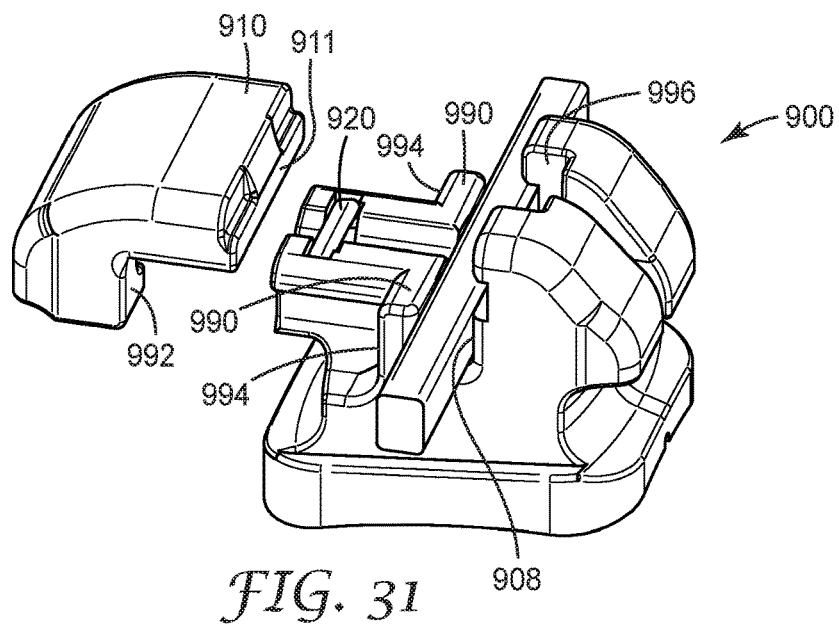
FIG. 31 is an exploded perspective view of an orthodontic appliance engaging an archwire according to another embodiment, looking toward its facial, distal, and gingival sides.
Figure 32:
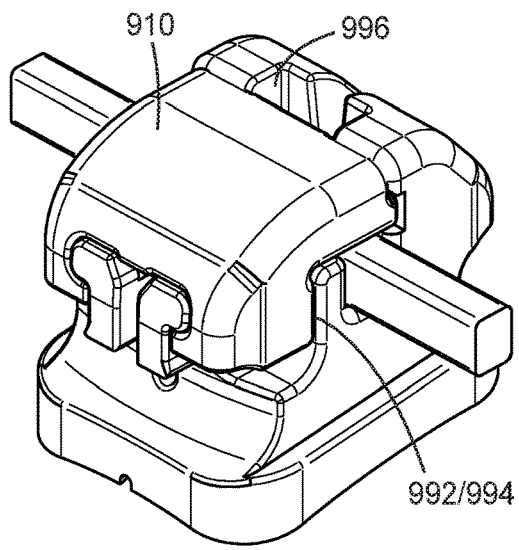
FIG. 32 is a perspective view of the appliance of FIG. 31, looking toward its facial, distal, and occlusal sides.
Figure 33:
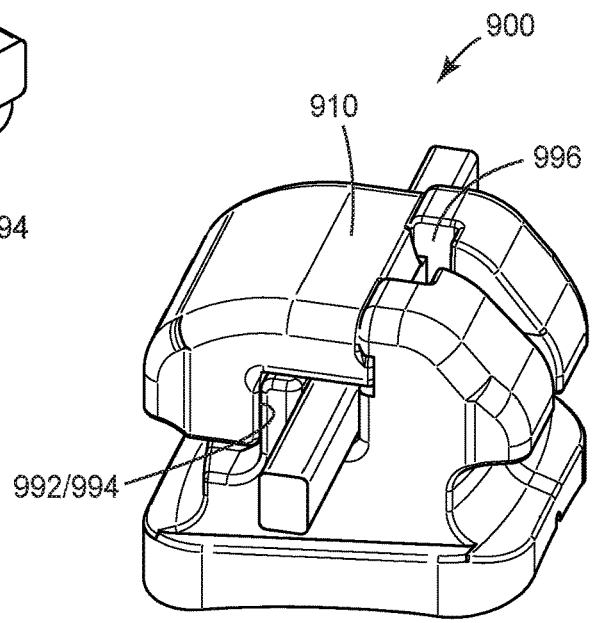
FIG. 33 is a perspective view of the appliance of FIG. 31-32, looking toward its facial, distal, and gingival sides.

FIGS. 31-33 show an appliance 900 in disassembled and assembled views according to yet another exemplary embodiment. This embodiment further develops the concept of an integral wall aligned along the gingival side of an archwire slot 908 and includes a feature to facilitate operation of the ligating mechanism. The appliance 900 bears essentially the same features as those of appliance 800, but includes a wall 990 that is integral with the appliance body and defines the gingival (or occlusal-facing) side of the archwire slot 908. In a preferred embodiment, the wall 990 extends along essentially the entire mesial-distal length of the archwire slot 908. Advantageously, the archwire slot 908 is highly rigid, since each of the three sides of the archwire slot 908 is substantially defined by the body of the appliance 900 along the mesial-distal length of the archwire slot.

The appliance 900 includes a door 910 akin to that of appliance 800, but a gingival-facing surface 992 of the door 910 flatly abuts an opposing occlusal-facing surface 994 of the wall 990 when the door 910 is in its closed position as shown in FIGS. 32-33.

Having the wall 990 extend along the mesial-distal length of the archwire slot 908 is significantly advantageous because it prevents a ligated archwire from imparting significant occlusal or gingival (i.e. sliding) forces to the door 910. As shown in FIGS. 31-33, the archwire slot 908 is bounded on three of its four sides by the appliance body, and each of the three sides extends essentially along the entire mesial-distal length of the archwire slot. On the fourth side, only the labial-facing side of the door 910 can contact an archwire captured in the archwire slot 908. Consequently, there is great freedom for the archwire to deliver substantial tipping and torque forces to the appliance 900 while avoiding the possibility of the door 910 unexpectedly opening during the course of treatment.

The wall 990, as shown, has generally parallel opposing walls facing occlusal and gingival directions. As an option however, the wall 990 could be tapered or thickened along some regions to increase strength. For example, the mesial and distal ends of the wall 990 could have greater occlusal-gingival thickness relative to the thickness along centrally located areas of the wall 990. In some of these embodiments, the mating surfaces 992, 994 could extend along a curved topology in an interlocking configuration to help prevent wobbling of the door 910 when closed.

As an added optional feature, the appliance 900 includes a rectangular recess 996, located at the seam between the leading, occlusal edge of the door 910 and appliance body. The recess 996 allows for insertion of a suitable flat-ended hand instrument to assist in opening of the door 910. Once inserted, the instrument can be rotated 90 degrees about its long axis, thereby operating as a cam for slidably opening the door 910. In the embodiment shown, the occlusal edge of the door 910 (bounding the recess 996) tapers to a pre-defined engagement surface 911 that extends along a mesial-distal direction adjacent the bottom of the recess 996. The engagement surface 911 is suitably positioned to enable the instrument to transmit forces to slide the door 910 open and avoid transmitting a moment which could cause the door 910 to rotate and/or jam.

Options and advantages broadly related to this concept are disclosed, for example, in U.S. Pat. No. 6,506,049 (Hanson) and U.S. Patent Publication No. 2009/0004618 (Oda, et al.).

Referring to FIG. 31, the appliance 900 further includes a beam 920 having functional features related to that of the beam 720 in the appliance 700. In a manner similar to the beam 720, the beam 920 mechanically interacts with a pair of protrusions (not visible) situated on the lingual-facing side of the door 910 to toggle the door between open and closed positions, while also preventing the door 920 from becoming accidently disengaged from the rest of the appliance 900. Optionally and as shown, the beam 920 has a generally rectangular cross-section with rounded corners. In this embodiment, the rounded corners have radii such that two of the four sides of the cross-section are curved across essentially their entire length, thereby facilitating the opening and closing of the door 920. The beam 920 is also oriented at a characteristic tilt angle, as described previously with respect to beam 620a.

Further aspects concerning the configuration and operation of the appliances 800, 900 are generally analogous to those of appliances already described (e.g. appliances 500, 600, 700) and will not be revisited here.

Kits and assemblies of the appliance described are also contemplated herein. For example, one or more of the appliances described herein may be pre-coated with a suitable orthodontic adhesive and packaged in a container or a series of containers, as described for example in U.S. Pat. No. 4,978,007 (Jacobs et al.); U.S. Pat. No. 5,015,180 (Randklev); U.S. Pat. No. 5,429,229 (Chester et al.); and U.S. Pat. No. 6,183,249 (Brennan, et al.), and U.S. Patent Publication No. 2008/0286710 (Cinader et al.) As another option, any of these appliances could also be used in combination with a placement device allowing for indirect bonding to the patient, as described in U.S. Pat. No. 7,137,812 (Cleary, et al.).

As a further option, any of the above appliances may include an archwire slot that has opposing sidewalls that are tapered to enhance torque strength, as described in pending provisional U.S. Patent Application Ser. No. 61/545,361 (Yick et al.).

Additional embodiments of the present invention are herein enumerated as follows:

A. An orthodontic appliance comprising: a base; a body extending outwardly from the base; an archwire slot extending across the body in a generally mesial-distal direction; a recess located on the body adjacent the archwire slot; a retention member received in the recess, the retention member dividing the recess into at least first and second regions; and a door slidably engaged to the body and having a protrusion, the protrusion extending into the first region when the door is open to allow access to the archwire slot and extending into the second region when the door is closed to prevent access to the archwire slot.

B. The appliance of embodiment A, wherein the recess has a bottom wall and opposing first and second side walls.

C. The appliance of embodiment A or B, the retention member comprising: a first beam; and
a second beam spaced apart from the first beam along a generally occlusal-gingival direction, wherein each beam extends along a generally mesial-distal direction, the first region is located between the first and second beams, and the second region is located on the occlusal or gingival side of both the first and second beams.

D. The appliance of embodiment C, wherein the first beam has a generally rectangular cross-section and the second beam has a generally circular cross-section.

E. The appliance of any one of embodiments A-D, wherein at least one beam has a generally curved configuration along its longitudinal direction.

F. The appliance of embodiment A or B, wherein the protrusion is a first protrusion and wherein the door further comprises a second protrusion spaced from the first protrusion along the sliding direction of the door, whereby the first and second protrusions reside in respective second and first regions when the door is open and the first and second protrusions both reside in the second region when the door is closed.

G. The appliance of any one of embodiments A-F, wherein the archwire slot is bounded along three sides in a generally rectilinear configuration, each side substantially defined by the body along the mesial-distal length of the archwire slot.

H. An orthodontic appliance comprising: a base; a body extending outwardly from the base; an archwire slot extending across the body in a generally mesial-distal direction; a recess located on the body adjacent the archwire slot, the recess having a bottom wall and opposing first and second side walls; a retention member received in the recess; and a door slidably engaged with the body and having a protrusion extending into the recess, the retention member resiliently deflecting to toggle the protrusion between a first position wherein the door is open to allow access to the archwire slot and a second position wherein the door is closed to prevent access to the archwire slot.

I. The appliance of embodiment A, B, G, or H, the retention member further comprising: a center section extending along the bottom wall and having first and second ends; an arched section joined at the first end; and a tail section joined at the second end and extending at an acute angle relative to the center section, the first position located between the first side wall and the arched section, and the second position located between the arched section and the second side wall.

J. The appliance of embodiment A, B, G, or H, wherein the retention member is generally coplanar with the bottom wall and resiliently deflects in a direction transverse to the sliding direction of door.

K. The appliance of embodiment J, wherein the retention member has a generally "U"-shaped configuration.

L. The appliance of embodiment J or K, wherein the retention member further comprises a pair of interior side surfaces and a pair of opposing inward-facing projections disposed on the side surfaces between the first and second regions.

M. An orthodontic appliance comprising: a base; a body extending outwardly from the base;

an archwire slot extending across the body in a generally mesial-distal direction; a recess located on the body adjacent the archwire slot, the recess having a bottom wall and opposing first and second side walls; a retention member received in the recess, the retention member comprising: a center section extending along the bottom wall and having first and second ends; an arched section joined to the first end and having an apex; and a tail section joined to the second end and extending at an acute angle relative to the center section; and a door slidably engaged with the body and having a protrusion extending into the recess, wherein the protrusion resides between the first side wall and the arched section when the door is open to allow access to the archwire slot and the protrusion rests between the arched section and the second side wall when the door is closed to prevent access to the archwire slot.

N. The appliance of any one of embodiments B-M, the recess further comprising opposing third and fourth side walls, wherein the first, second, third, and fourth side walls retain the retention member and constrain sliding of the retention member in directions generally parallel to the bottom wall.

O. The appliance of any one of embodiments A-N, wherein the retention member comprises a shape memory alloy.

P. The appliance of any one of embodiments A-O, wherein the retention member is a unitary component.

Q. The appliance of any one of embodiments A-P, wherein each of the base, body, and door comprises a translucent ceramic material.|

R. The appliance of any one of embodiments A-Q, wherein the door and protrusion are a unitary component.

S. The appliance of any one of embodiments A-R, wherein the protrusion has a generally planar front face and back face, the front and back faces being oriented at different angles relative to the bottom wall of the recess.

T. The appliance of any one of embodiments I and M-S, wherein the center section, arched section, and tail section are integral components of the retention member.

U. The appliance of any one of embodiments I and M-T, wherein the tail section has a cross-sectional dimension that generally decreases with increasing distance from the center section.

V. The appliance of any one of embodiments A-U, wherein the body has an opening in communication with both the recess and an exterior of the appliance, the opening being sufficiently sized to enable passage of the protrusion through the opening and into the recess when assembling the door to the body.|

W. The appliance of any one of embodiments I and M-V, wherein the spacing between the arched section and the opposing side walls is sized whereby the retention member is maintained in a state of compressive stress.

X. The appliance of any one of embodiments A-W, wherein the body further comprises a pair of opposing grooves, and the door comprises a pair of rails slidably received in the pair of grooves.

Y. The appliance of embodiment A-X, wherein the door has a mesial-distal width that substantially matches the overall mesial-distal width of the appliance.

Z. A method of assembling an orthodontic appliance having ceramic body, a ceramic door having a protrusion, and a retention member, the method comprising: placing the retention member into a recess located in the body; slidably engaging the door along a pair of rails disposed on the body until the protrusion contacts an exterior surface of the retention member; and urging the door against the retention member until the protrusion is received within a region of the recess that is at least partially defined by the combination of the recess and an interior surface of the retention member.

AA. The method of embodiment Z, wherein the retention member comprises a pawl that resiliently deflects to enable assembly of the door to the body and subsequently engages a side wall of the recess to prevent spontaneous disassembly.

All of the patents and patent applications mentioned above are hereby expressly incorporated into the present description. The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

What is claimed is:

1. An orthodontic appliance comprising:
a base;
a body extending outwardly from the base;
an archwire slot extending across the body in a generally mesial-distal direction;
a recess located on the body adjacent the archwire slot;
a retention member received in the recess, the retention member dividing the recess into at least first and second regions, wherein the retention member comprises a first beam extending along a mesial distal direction; and
a door slidably engaged to the body and having a first protrusion, wherein the first protrusion comprises a generally trapezoidal profile as viewed from the mesial or distal direction, the first protrusion having a gingival-facing edge forming a first sidewall angle $\beta_1$ and an occlusal-facing edge forming a second side-wall angle $\beta_2$, the first protrusion extending into the first region when the door is open to allow access to the archwire slot and extending into the second region when the door is closed to prevent access to the archwire slot.

2. The appliance of claim 1, wherein the recess has a bottom wall and opposing first and second side walls.

3. The appliance of claim 1, wherein the first beam has a curved configuration along some or all of its length.

4. The appliance of claim 1, wherein the first beam is a round beam.

5. The appliance of claim 1, wherein the first beam is a rectangular beam.

6. The appliance of claim 5, wherein the rectangular beam extends along an axis oriented at an angle $\theta$ relative to the sliding direction the door, wherein the angle $\theta$ is at least about 0.1 degrees.

7. The appliance of claim 6, wherein the angle θ is about 90 degrees or less.

8. The appliance of claim 1, further comprising a second beam spaced apart from the first beam along a generally occlusal-gingival direction, wherein each beam extends along a generally mesial-distal direction, the first region is located between the first and second beams, and the second region is located on the occlusal or gingival side of both the first and second beams.

9. The appliance of claim 8, wherein the first beam has a generally rectangular cross-section and the second beam has a generally circular cross-section.

10. The appliance of claim 9, wherein the rectangular beam extends along an axis oriented at an angle θ relative to the sliding direction the door, wherein the angle θ is at least about 0.1 degrees.

11. The appliance of claim 10, wherein the angle θ is about 90 degrees or less.

12. The appliance of claim 9, wherein the second beam is spaced from the first beam toward the gingival direction.

13. The appliance of claim 12, wherein first side wall angle $\beta_1$ is less than the second sidewall angle $\beta_2$.

14. The appliance of claim 1, wherein the first beam comprises a superelastic nickel-titanium alloy.

15. The appliance of claim 1, wherein the generally trapezoidal profile is an asymmetric trapezoidal profile.

16. The appliance of claim 1, further comprising a second protrusion spaced from the first protrusion along the sliding direction of the door, whereby the first and second protrusions reside in respective second and first regions when the door is open and the first and second protrusions both reside in the second region when the door is closed.

* * * * *

UNITED STATES PATENT AND TRADEMARK OFFICE
CERTIFICATE OF CORRECTION

PATENT NO. : 10,064,705 B2  
APPLICATION NO. : 15/651726  
DATED : September 4, 2018  
INVENTOR(S) : Lee Yick et al.

Page 1 of 1

It is certified that error appears in the above-identified patent and that said Letters Patent is hereby corrected as shown below:

Column 1  
Line 2, below "SELF-LIGATING ORTHODONTIC BRACKET" insert -- CROSS REFERENCE TO RELATED APPLICATIONS This application is a continuation of U.S. Application ser. No. 14/416,113, filed Jan. 21, 2015, now pending, which is a 371 of international Application ser. No. PCT/US2013/028785, filed Mar. 4, 2013, which claims benefit of provisional Application ser. No. 61/674,620, filed Jul. 23, 2012, the disclosures of which are incorporated by reference in their entirety herein. --, therefor.

Column 4  
Line 57, delete "FIG." and insert -- FIGS. --, therefor.  
Line 66, delete "FIG." and insert -- FIGS. --, therefor.

Column 9  
Line 2, delete "constrast," and insert -- contrast, --, therefor.

Column 13  
Line 67, after "direction" insert -- of --.

Column 19  
Line 48, delete "material.|" and insert -- material. --, therefor.  
Line 67, delete "body.|" and insert -- body. --, therefor.

Column 20  
Line 66, in Claim 6, after "direction" insert -- of --.

Column 21  
Line 16, in Claim 10, after "direction" insert -- of --.

Signed and Sealed this  
Twenty-seventh Day of November, 2018

Andrei Iancu  
*Director of the United States Patent and Trademark Office*